United States Patent [19]

Ryan et al.

[11] Patent Number: 4,563,305

[45] Date of Patent: Jan. 7, 1986

[54] RADIOLABELLED SUBSTRATES FOR ASSAYING MAMMALIAN ENZYMES

[75] Inventors: James W. Ryan; Alfred Chung, both of Miami, Fla.

[73] Assignee: University of Miami, Miami, Fla.

[21] Appl. No.: 222,980

[22] Filed: Jan. 7, 1981

[51] Int. Cl.$^4$ ............................................. C07C 103/52
[52] U.S. Cl. ............................................. 260/112.5 R
[58] Field of Search ...................... 435/7; 260/112.5 R

[56] References Cited

U.S. PATENT DOCUMENTS

| | | | |
|---|---|---|---|
| 4,231,999 | 11/1980 | Carlsson et al. | 435/7 |
| 4,289,748 | 9/1981 | Harris et al. | 435/7 |
| 4,327,178 | 4/1982 | Ryan et al. | 260/112.5 R |
| 4,331,646 | 5/1982 | Delaage | 260/112.5 R |

OTHER PUBLICATIONS

Charles W. Parker, "Radioimmunoassay of Biologically Active Compounds" (1976) pp. 68–79, Ch. 5.

Primary Examiner—Delbert R. Phillips

[57] ABSTRACT

Compounds which are substrates for mammalian enzymes, especially proteolytic and peptidase enzymes, are disclosed. These compounds, in general, have the general formula X-T, W-Y or X-(Pep)-Y, wherein X is a radiolabelled benzoyl or hydroxyphenylpropanoyl group, T is the —NH residue of a known chromogenic or fluorogenic substrate comprising at least one amino acid group which may be substituted with other organic groups, Y is a radiolabelled benzylamine group, W is the

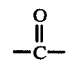

residue of a known chromogenic or fluorogenic substrate comprising at least one amino acid group which may be substituted with other organic groups, and (Pep) is a difunctional or polyfunctional residue from a known chromogenic or fluorogenic substrate comprising at least two amino acid groups in peptide linkage, which residue may be substituted with other organic groups. These substrates exhibit many advantages over the chromogenic and fluorogenic analogs, including greater sensitivity, surprising and unpredictable affinity and specificity, and the like.

18 Claims, No Drawings

RADIOLABELLED SUBSTRATES FOR ASSAYING MAMMALIAN ENZYMES

BACKGROUND OF THE INVENTION

The present invention relates to synthetic substrates which are to be used as reagents for the assay of various mammalian enzymes. More particularly, it relates to synthetic substrates containing a radiolabel which are especially useful in radioassays for proteolytic and peptidase enzymes.

Each of the substrates according to the invention is especially suitable for quantitative determination of one or more of the enzymes discussed herein. Further, each of the substrates can be used for a study of reactions in which an enzyme is formed, inhibited or consumed, or for determination of factors influencing or taking part in such a reaction. Synthetic substrates for enzyme determination have great advantages as compared to the natural ones, provided that they fulfill certain conditions, such as affinity for the enzyme, sensitivity and specificity for the enzyme, solubility in water or other biological test liquid and easy detectability of at least one of the remnants obtained upon hydrolytic cleavage.

The following abbreviations are used herein:
Ala alanine
Aoc amyloxycarbonyl
Arg arginine
Asn asparagine
Asp aspartic acid
Aze 2-azetidine carboxylic acid
Boc t-butyloxycarbonyl
Bz benzoyl
cpc cyclopentanecarbonyl
Cys cysteine
Dns dansyl
Gln glutamine
Glu glutamic acid
<Glu pyroglutamic acid
Gly glycine
His histidine
Ile isoleucine
Leu leucine
Lys lysine
Met methionine
MNS 4-methoxy-2-naphthyl-amide
Nle norleucine
Orn ornithine
Phe phenylalanine
Sar sarcosine
Pip pipecolic acid
Pro proline
ΔPro 3,4-dehydroproline
Ser serine
Thr threonine
Trp tryptophan
Tyr tyrosine
Val valine
Z benzyloxycarbonyl
Cbo=CbO carbobenzoxy All amino acids are in the L-form unless otherwise indicated. The enzyme nomenclature developed by the Enzyme Committee of the International Union of Biochemistry is used herein.

Recently, many synthetic peptide substrates have been prepared for different proteolytic enzymes. These substrates have generally included a chromogenic or fluorogenic group for measuring the amount of substrate hydrolysis by a particular enzyme or class of enzymes. For example, U.S. Pat. No. 3,886,136 discloses several chromogenic substrates for assaying enzymes of the class E.C. 3.4.4 (now class E.C. 3.4.21). Examples of this class include trypsin (E.C. 3.4.21.4), chymotrypsin (E.C. 3.4.21.1), plasmin (E.C. 3.4.21.7) and thrombin (E.C. 3.4. 21.5), among others. The substrates disclosed in this patent have the general formula:

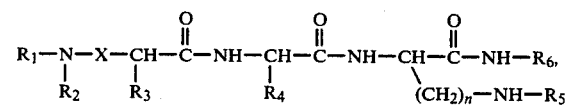

wherein $R_3$ and $R_4$ are alkyl groups having 3–8 carbons, $R_4$ can also be benzyl or phenyl, $R_5$ is hydrogen or

n is 2,3 or 4, $-NH-R_6$ is the chromogenic group, X is $CH_2$ or a single bond, and $R_1$ and $R_2$ can be selected from a variety of groups which is not critical to this discussion. U.S. Pat. No. 4,016,042 discloses chromogenic or fluorogenic substrates for proteolytic enzymes of the class E.C. 3.4.21. These substrates are derivatives of Pro-X-Y-R where X is Phe, Tyr, phenylglycine or β-cyclohexylalanine, Y is Arg or Lys and R is the chromogenic or fluorogenic group.

U.S. Pat. No. 4,061,625 discloses several chromogenic substrates useful for assaying thrombin (E.C. 3.4.21.5) or thrombin-like enzymes. These substrates have the formula (D) $A_1$-$A_2$-Arg-R where $A_1$ is Phe or Tyr, $A_2$ is Aze, Pro or Pip, and R is the chromogenic group. In these substrates the symbol (D) $A_1$ signifies that $A_1$ is in the D form but $A_2$ and Arg are in the L-form. This symbolism is used throughout this application.

U.S. Pat. No. 4,070,245 discloses several chromogenic or fluorogenic substrates useful for assaying enzymes of the class E.C. 3.4.21. These substrates are derivatives of Gly-Pro-X-R where X is Lys or Arg and R is a chromogenic or fluorogenic group.

U.S. Pat. No. 4,137,225 discloses chromogenic substrates for proteases (serine proteases) of the class E.C. 3.4.21. This patent discloses substrates of the formula (D)$A_1$-$A_2$-$A_3$-R where $A_1$ and $A_2$ are selected from the group of amino acids Gly, Ala, Val, Leu, Ile, Pip, Pro or Aze, $A_2$ can also be Phe, $A_3$ is Arg, Lys or Orn and R is the chromogenic group.

U.S. Pat. No. 4,147,692 discloses a fluorogenic substrate, Gly-Pro-R where R is the fluorogenic group, for assaying the enzyme X-prolyl dipeptidyl aminopeptidase. U.S. Pat. No. 4,119,620 also discloses substrates for the enzyme X-prolyl dipeptidyl aminopeptidase. These substrates have the general formula X-Pro-Y wherein X can be any amino acid and Y is a chromogenic group.

U.S. Pat. No. 4,188,264 discloses several chromogenic or fluorogenic substrates for the clotting enzyme of horseshoe crabs. These substrates have the general formula $R_1$-Gly-Arg-$R_2$ wherein $R_1$ is selected from the group comprising N-protected L-amino acids, N-protected L-peptides, (D)amino acid-L-amino acid or (D) amino acid-L-peptide and $R_2$ is the chromogenic or fluorogenic group.

U.S. Pat. No. 4,028,318 discloses chromogenic substrates for serine proteases (E.C. 3.4.21.) especially factor Xa (E.C. 3.4.21.6). These substrates have the general formula R-A$_1$-A$_2$-Gly-Arg-R$_1$ where A$_1$ may be a single bond or Gly, Ala, Val, Leu, Ile, Pro, Met, Phe or Tyr, A$_2$ may be Glu, Gln, Asp or Asn, R is H or a blocking group and R$_2$ is the chromogenic group.

U.S. Pat. No. 4,056,519 discloses fluorogenic substrates for the enzyme, plasmin (E.C. 3.4.21.7.). These substrates have the general formula

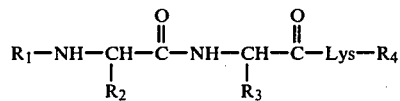

wherein R$_1$ is benyloxycarbonyl, R$_4$ is 4-methoxy-2-naphthylamine (MNA), R$_2$ and R$_3$ may be H, alkyl, hydroxyalkyl, mercaptoalkyl, methylthioalkyl, benzyl or hydroxybenzyl. The preferred substrates are Z-Gly-Gly-Lys-MNA or Z-Ala-Ala-Lys-MNA.

Other U.S. patents which disclose chromogenic or fluorogenic peptide substrates include the following: Nos. 3,144,484 for trypsin (E.C. 3.4.21.4); 3,536,588 for Leu aminopeptidase (E.C. 3.4.11.1); 3,591,459 for amino acid arylamidase; 3,607,859 for neutral protease (microbial metalloenzymes, E.C. 3.4.23.4); 3,703,441; 3,769,173; 3,773,626; 3,892,631 and 4,177,109 for γ Glu transpeptidase (E.C. 2.3.2.2); 3,745,212 for pancreatic endopeptidases; 3,884,896, 4,191,808 and 4,191,809 for peptide peptidohydrolases such as class E.C. 3.4.21; 4,046,633 for renin (E.C. 3.4.99.19); 4,108,726 and 4,115,374 for angiotensin converting enzyme (peptidyl-dipeptide hydrolase, E.C. 3.4.15.1); 4,116,774 for Leu aminopeptidase, Cys aminopeptidase (E.C. 3.4.11.3) and γ-Glu transpeptidase; 4,138,394 for collagenase (E.C. 3.4.24.3); and 4,207,232 for factor Xa (E.C. 3.4.21.6). U.S. Pat. Nos. 3,862,011; 4,155,916 and 4,167,449 contain tables listing specific chromogenic or fluorogenic substrates for various proteolytic enzymes. Still further colorometric substances useful for assaying one or more of thrombin, horesehoe crab coagulating enzyme, urokinase or Factor XIIA are shown in U.S. Pat. No. 4,215,047. Further substrates for thrombin and trypsin-like enzymes are shown in U.S. Pat. Nos. 4,217,269, 4,219,497 and 4,221,706. U.S. Pat. No. 4,216,142 describes substrates especially useful with the enzyme inhibitor antithrombin III.

In addition to the above-identified U.S. patents, chromogenic or fluorogenic peptide substrates for various proteolytic enzymes have also been described in many literature articles. Representative articles which refer to enzymes not previously discussed herein include the following: Yoshimota et al., *Biochim. Biophys. Acta* 569, 184 (1979) for post-proline cleaving enzyme (E.C. 3.4.21.-) using Z-Gly-Pro-R$_1$ wherein R$_1$ is a chromogenic or fluorogenic group as the substrate; Grant et al., *Biochim. Biophys. Acta* 567, 207 (1979) for enterokinase (E.C. 3.4.21.9) using Gly-(Asp)$_4$-Lys-naphthylamide; Reilly et al., *Biochim. Biophys. Acta* 621, 147 (1980) for elastase (E.C. 3.4.21.11) using succinyl-(Ala)$_3$-p-nitroanilide; Pozgay et al, *Eur. J. Biochem* 95, 115 (1979) for Subtilisin Carlsberg (E.C. 3.4.21.14) using, for example, Z-Arg-(Nle)$_2$-p-nitroanilide; and, Lojda, *Histochem.* 64, 205 (1979) for brush border endopeptidase using glutaryl-(Ala)$_3$-MNA or succinyl-(Ala)$_3$-l-naphthylamide.

There are many disadvantages in the use of the chromogenic and fluorogenic substrates of the prior art for the assay of mammalian enzymes, especially proteolytic and peptidase enzymes. The chromogenic assays frequently use a substrate that reacts with a given enzyme to release p-NO$_2$-aniline as the chromophore. p-NO$_2$-aniline has a low molar extinction coefficient, thus a high concentration of substrate is required in order to permit formation of sufficient product for accurate and precise measurement. This requirement for high substrate concentration is disadvantageous; the substrates are often very expensive to make. In addition, solubility of these substances in buffer is often low. Some of the chromogenic substrates (e.g. benzoyl-Phe-Val-Arg-p-NO$_2$-anilide and (D)Phe-Pip-Arg-p-NO$_2$-anilide) cannot be dissolved in their reaction buffers at concentrations high enough to allow the enzyme-substrate reaction to proceed under conditions of zero order reaction kinetics (i.e. under conditions wherein a substantial excess of substrate is present). See Lehninger, A., *Biochemistry* (1970) p. 153 et seq. In consequence, some of the chromogenic substrates must be used at concentrations within the range of mixed first order and zero order enzyme kinetics. Use of these substrates at concentrations appropriate to first order kinetics is often infeasible because the color produced is often so weak that it cannot be detected, even instrumentally, unless the sample is colorless. Even at the concentrations used, it is often necessary to employ special techniques, e.g. sonication, heating at 50° C., etc. to effect dissolution of the p-nitroanilide containing substrate.

There are still other disadvantages of the p-nitroaniline-labeled chromogenic substrates. The amide bond formed between an amino acid residue of a given substrate and p-NO$_2$-aniline to yield the corresponding p-NO$_2$-anilide is relatively unstable and can undergo spontaneous hydrolysis at pH 9 and higher pH's. The spontaneous hydrolysis is particularly disadvantageous for the assay, e.g., of human glandular kallikreins, and other enzymes having pH optima within the range of pH 9 to 10. Still a further problem with this type of substrate is that the chromophoric reaction product, p-NO$_2$-aniline, is not stable and is readily oxidized. Thus, the measurement must be made immediately or accuracy is lost.

A further disadvantage of the p-nitroanilide substrates is that they are not stable under ordinary ambient conditions and are especially prone to oxidative degradation. As a result, special storage conditions are needed. Moreover, the instability problems are such that precise repetition of substrate in different batch preparations is difficult to achieve and may often not occur. This in its turn causes quality control problems in the marketplace. Even using the same batch, moreover, repetitive analyses conducted days or weeks apart may field varying results due to instability and interim degradation of the substrate.

Others of the chromogenic substrates (e.g., benzoyl-Pro-Phe-Arg-p-NO$_2$-anilide) have been thought to be unreactive with a given enzyme (e.g., the last-mentioned substrate with human urinary kallikrein), whereas in fact the substrates have a high affinity (low K$_m$) for their designated enzymes and a relatively low maximum velocity of reaction (V$_{max}$). Because of the low V$_{max}$, insufficient chromophore is generated to allow its measurement. Not uncommonly, the substrates of high affinity and low V$_{max}$ also inhibit the activity of the enzyme to be measured (so-called substrate inhibition) at substrate concentrations only slightly greater than $K_m$. Thus, Chung et al, Adv. Experimental Med. and Biol., 120A, 115–125 (1979) have shown that the $K_m$ of reaction of human urinary kallikrein with Pro-Phe-Arg-[$^3$H]benzylamide is 3 μM, and substrate inhibition is manifest at 5 μM.

The sensitivity of chromogenic substrates for proteolytic and peptidase enzymes is often low. In consequence, it may be difficult or impossible to assay an enzyme present in minute quantity. As for other assays of enzymic activity, sensitivity is in large part a function of the ratio of $V_{max}/K_m$ and the detectability of the product. As noted above, solubility of the substrate may compromise sensitivity of an assay when a sufficient substrate concentration cannot be obtained to allow velocity of the reaction to approximate $V_{max}$. Since the detectability of the chromophoric product is in general poor, it is often necessary to use a substrate of relatively low affinity (high $K_m$) and high $V_{max}$ in order to develop a practical chromogenic assay. Typically, substrates of high affinity provide the greatest specificity or selectivity of reaction. Hence, some chromogenic assays must use substrates of less than optimum specificity for their designated enzymes in order to allow for the generation of sufficient chromophore for accurate measurement.

Chromophores other than p-NO$_2$-aniline can, in principle, be used. However, the substitution of one leaving group for another often results unpredictably and for unknown reasons, in sensitivity, specificity and other differences. Chromophoric substitution may make the resulting substrate more or less sensitive or more or less specific than the corresponding p-NO$_2$-anilide substrate. For example, we have found that Pro-Phe-Arg-anilide has a lower $K_m$ and a higher $V_{max}$ on reaction with human urinary kallikrein than does Pro-Phe-Arg-benzylamide. Further, neither aniline nor benzylamine is a strong chromophore; both are far more difficult to detect colorimetrically than p-NO$_2$-aniline. Even more marked changes have been encountered. For example, benzoyl-Val-Gly-Arg-p-NO$_2$-anilide and <Glu-Gly-Arg-p-NO$_2$-anilide are reactive with human urokinase, but the corresponding benzylamides are not reactive with urokinase and are highly reactive with the clotting enzyme of the horseshoe crab.

Some chromophores, e.g., β-naphthylamine, are more readily detected than is p-NO$_2$-aniline but may be carcinogenic. Other chromophores, e.g., p-NO$_2$-phenol, are as difficultly detected as is p-NO$_2$-aniline. These chromophores are incorporated into a given substrate via an ester linkage and have the expected advantages and disadvantages. Typically, the reaction of a p-NO$_2$-phenyl ester with a given enzyme has a significantly higher $V_{max}$ than does the reaction using the same enzyme and the corresponding p-NO$_2$-anilide substrate. However, spontaneous hydrolysis of the ester substrate becomes serious at pH levels above 7.0. Thioester chromogenic substrates have similar advantages and disadvantages. Both ester and thioester substrates may under some conditions behave as active esters and hence irreversibly inhibit the enzyme to be assayed.

Additional known chromophores, such as hydroxycoumarins and methylcoumarins, share the solubility, affinity, detectability, cost, and other disadvantages of p-nitroaniline, albeit not necessarily to the same degree when otherwise analogous substrates are compared.

Fluorogenic substrates have many of the same disadvantages as the chromogenic substrates. Fluorogenic substrates generally use a derivative of naphthylamine in either amide or ester linkage. More recently, substrates have been designed to contain a coumarin derivative as the fluorogenic moiety. As noted above, the naphthylamine derivatives may be carcinogenic. Apparently, the substrates and their fluorescent products are not stable as judged by the manufacturers' recommended storage precautions for these compounds. Fluorogenic substrates as a class are even less soluble than the corresponding p-NO$_2$-anilides, and it is frequently necessary first to dissolve a given fluorogenic substrate in an organic solvent such as DMSO (dimethylsulfoxide) before adding the substrate to a buffered aqueous solution compatible with the enzyme-substrate reaction. The organic solvent may damage or partially denature the enzyme to be measured. Even if the denaturation of enzyme is slight, extensive controls must be inserted in the assay protocol in order to retain adequate precision and accuracy. Some fluorogenic substrates are not highly soluble even in an organic solvent. Thus, the assistance of the organic solvent may not suffice to yield a substrate concentration in the reaction mixture adequate to support a reaction obeying zero order enzyme kinetics. Consequently, many fluorogenic assays use substrate concentrations between the ranges of first order and zero order enzyme kinetics. The fluorophoric leaving groups used at present are even less soluble in aqueous solution than their parent substrates and may tend to precipitate as the enzyme-substrate reaction progresses. A disadvantage unique to fluoroscence assays is self-quenching of fluorescence. Further intrinsic fluoroscence of some biological fluids may equal or exceed in intensity that of the fluorophor released from a given substrate. The intensity of the intrinisic fluoroscence of biological specimen varies widely; hence, any specimen may differ markedly from another, even of the same type.

Information on aspartyl-$^3$[H]-benzylamide as a substrate for angiotensin aminopeptidase and lysine-$^3$[H]-benzylamide as a substrate for kinin, converting enzyme (a carboxypeptidase enzyme) was made publicly available through National Institutes of Health channels, on behalf of the present inventors in 1979. This work was preliminary to the present invention. A pertinent publication emanating from this laboratory and describing substrate work of these inventors within the scope of this invention is Ryan, W. and Ryan, U.S., "Biochemical and Morphological Aspects of the Actions and Inactivation of Kinins and Angiotensins" contained in *Enzymatic Release of Vasoactive Peptides,* edited by F. Gross and G. Vogel, published mid-1980. The article additionally makes reference to tritiated benzoyl derivatives of the tripeptides Gly-Gly-Gly, Gly-His-Leu, Pro-Phe-Arg, Phe-His-Leu and Phe-Ala-Pro as angiotensin converting enzyme substrates and to the compound Pro-Phe-Arg-$^3$[H] benzylamide as a glandular kallikrein substrate.

The present invention obviates the disadvantages of the prior art colorometric and fluorometric substrates by providing a class of radiolabelled compounds, each member of which is useful as an assay substrate for one or more proteolytic or peptidase enzymes. Each of the compounds of the invention is a radiolabelled benzoyl, p-OH-phenyl-propanoyl or benzylamide derivative of an amino acid or oligopeptide. In each instance, the benzoyl, p-OH-phenyl-propanoyl or benzylamide moiety contains the radiolabel. The radiolabelled moieties allow the highly sensitive detection of a given substrate or one of the products formed by enzymic hydrolysis, or both. Thus, enzymic activity can be measured at high sensitivity in terms of the rate of substrate utilization and/or product formation. In addition, the radiolabelled substrates and their cleavage products are stable compounds. The substrates, properly stored, retain activity for at least about two years. They can be used at concentrations in the range of first order enzyme kinetics so that concentrations as low as 50 nM are conventional and solubility in test fluids is never a problem. In addition, since 25 mg. of a given radiolabelled substrate of this invention will theoretically provide about five million tests whereas the same quantity of present commercial colorimetric substrates, e.g. from Kabi AB or Pentapharm, would yield theoretically, about 500 tests and the commercial fluorogenic substrates from e.g. American Hospital Supply, Dade Reagents Division, would theoretically yield also about 500 tests, it is evident that the cost savings available according to this invention are significant.

The amino acid or oligopeptide present in each substrate of this invention was originally selected to favor the affinity and selectivity of binding of that substrate for a designated enzyme. Thus, a substrate such as tosyl-Gly-Pro-Arg-[$^3$H]benzylamide incorporates a tripeptide sequence of a known natural substrate for thrombin. In similar vein, [$^3$H]benzoyl-Phe-Arg was designed for carboxypeptidase B and related enzymes and <Glu-Gly-Arg-[$^3$H]benzylamide was designed for urokinase. It has unexpectedly been found, however, that the radiolabelled moieties and even the radiolabels per se may enhance or decrease the affinity, selectivity and even specificity of a given substrate for its designated enzyme. For example, <Glu-Gly-Arg-[$^3$H]benzylamide was found to be unreactive with urokinase, the enzyme for which the analogous colorimetric substrate is specific, but was highly reactive with the horseshoe crab clotting enzyme. Conversely, (D)Phe-Pro-Arg-[$^3$H]benzylamide was found to have a higher affinity (lower $K_m$) for thrombin than that reported for the corresponding p-NO$_2$-anilide. Similarly, it has unexpectedly been found that substitutions or additions distant from the cleavage site of the substrate may unpredictably influence the kinetic behavior of a given substrate. For example, the addition of a biotinyl group to (D)Phe-Pro-Arg-[$^3$H]benzylamide to yield biotinyl-(D)Phe-Pro-Arg-[$^3$H]benzylamide yields a substrate for thrombin less than half as reactive as (D)Phe-Pro-Arg-[$^3$H]benzylamide itself.

The substrates of the present invention may be utilized in concentrations well within the range of first order enzyme kinetics. These substrates, labelled at high specific radioactivity, can be used in nanomolar or subnanomolar quantities without compromising the detection of substrate utilization or product formation. The typical $K_m$ for reaction of these substrates with their designated enzymes ranges from 1 μM to 1 mM. Because of the ready detectability of each substrate and at least one of its cleavage products, the substrates of this invention can be used at concentrations below $K_m$ and well within the range of first order enzyme kinetics. Within the latter range, enzyme activity, expressed as percent utilization of substrate per unit time, becomes independent of the actual substrate concentration; and the resulting assay yields results both more accurate and precise than those conducted with substrate at a concentration within the range of mixed first and zero order enzyme kinetics. Other advantages have been found. Because low concentrations of substrate can readily be used, solubility of substrate poses no problem, and organic solvents are not needed. Further, substrate inhibition and product inhibition are far less likely to occur. On the other hand, these substrates can be used at concentrations greater than the range of first order kinetics, either by raising the concentration of the radiolabelled substrate itself or by adding the corresponding non-radiolabelled compound.

SUMMARY OF THE INVENTION

Compounds which are substrates for various mammalian enzymes, especially proteolytic and peptidase enzymes, are disclosed. These compounds are p-hydroxyphenylpropanoyl, benzylamide or benzoyl derivatives of amino acids or peptides, in which the p-hydroxyphenylpropanoyl, benzylamine or benzoyl moieties contain a radiolabel. Many of these substrates exhibit increased sensitivity relative to chromogenic and fluorogenic substrates known in the prior art.

DETAILED DESCRIPTION OF THE INVENTION

The compounds of this invention are substrates for proteolytic and peptidase enzymes. These compounds are based on substrates known in the prior art in which the chromogenic or fluorogenic group of the known substrate has been replaced by a p-hydroxyphenyl-propanoyl, benzoyl or benzylamide moiety containing a radiolabel. The radiolabel can be any conventional radiolabel such as $^3$H, $^{14}$C, $^{125}$I, $^{131}$I, and the like. It is preferable that the label be $^3$H.

The substrates disclosed herein are useful for assaying one or more of the enzymes indicated in Table 1. The enzyme numbers, if determined, are also given.

TABLE 1

| Enzyme | Enzyme Number |
|---|---|
| α-glutamyl transpeptidase | 2.3.2.2. |
| aminopeptidases | 3.4.11 |
| carboxypeptidases | 3.4.12 |
| chymotrypsin | 3.4.21.1 |
| trypsin | 3.4.21.4 |
| thrombin | 3.4.21.5 |
| factor Xa | 3.4.21.6 |
| plasmin | 3.4.21.7 |
| enterokinase (and related enzymes) | 3.4.21.9 |
| elastase (and related enzymes) | 3.4.21.11 |
| subtilisin | 3.4.21.14 |
| Cathepsin B | 3.4.22.1 |
| Cathepsin D | 3.4.23.5 |
| Collagenase (and related enzymes) | 3.4.24.3 |
| Urokinase (and related enzymes) | 3.4.99.26 |
| Brush Border Endopeptidase | 3.4.99.26 |
| Cathepsin G | |
| Cathepsin C | |
| Dipeptidyl Aminopeptidase I | |
| Dipeptidyl Aminopeptidase II | |
| Dipeptidyl Aminopeptidase III | |
| Dipeptidyl Aminopeptidase IV | |
| Horseshoe Crab clotting enzyme | |
| Post-proline cleaving enzyme | |
| X-prolyl dipeptidyl aminopeptidase | |
| Glandular kallikrein (includes at least urinary and pancreatic kallikrein) | |
| Plasma kallikrein | |
| Angiotensin converting enzyme | |
| oxytocinase | |
| neutral proteases | |
| Proline endopeptidase | |

Substrates included within the scope of this invention, arbitrarily grouped with the enzyme for which an analogous chromophoric or fluorophoric substrate is specific, are set forth in Table 2. As already noted, the substrates of the invention have, in many instances, been found to exhibit greater affinity, selectivity, or specificity for enzymes other than those with which the prior art associates the chromogenic or fluorogenic analog. Hence, Table 2 is not intended as a representation that substrates of this invention named therein necessarily have affinity, specificity or selectivity for the enzyme with which each is grouped. In the table, Y refers to a radiolabelled benzylamine moiety in amido linkage with carboxyl group of the amino acid or peptide, X, encompasses either a radiolabelled benzoyl or p-hydroxyphenyl propanoyl group in an amido linkage with an amino group of the amino acid or peptide, and R refers to an alkyl group of 1–5 carbon atoms. The compounds may be represented by general formulae X-T and W-Y wherein T and Y represent residues of known fluorogenic and chromogenic substrates, T being the -NH- residue and W the -C$^O$- residue, it being understood that W may not be a single aspartyl or lysyl group.

TABLE 2

A. γ-Glutamyl Transpeptidase γ-Glu-Y

B. Aminopeptidases and Related Enzymes

Tyr-Y
Met-Y
Arg-Y
<Glu-Y
Leu-Y
Phe-Y
Trp-Y
Ile-Y
Val-Y
Ala-Y
Pro-Y
Cys-Y
His-Y
S-(Bz)-Cys-Y
Leu-Y

C. Carboxypeptidases and Related Enzymes

X-Gly-Phe
X-Gly-Arg
X-Ala-Phe
X-Ala-Arg
X-Phe-Phe
X-Phe-Arg
X-Gly-Trp
X-Gly-Tyr
X-Gly-Ala
X-Gly-Lys
X-Ala-Trp
X-Ala-Tyr
X-Ala-Ala
X-Ala-Lys
X-Phe-Tyr
X-Phe-Trp
X-Phe-Ala
X-Tyr-Tyr
X-Trp-Tyr
X-Tyr-Trp
X-Trp-Trp
X-Tyr-Ala
X-Trp-Ala
X-Phe-Lys
X-Trp-Lys
X-Tyr-Lys
X-Gly-Phe

D. Chymotrypsin glutaryl-Phe-Y
succinoyl-Ala-Ala-Pro-Phe-Y
acetyl-Trp-Y
Ala-Ala-Phe-Y
R-Bz-Phe-Y
R-Bz-Phe-Gly-Gly-Y
R-Bz-Phe-Gly-Y
N-(Bz)-Tyr-Y
R-(N-acetyl)-Phe-Y
N-(Bz)-Trp-Y
R-Tyr-Y
α-Bz-Lys-Y
acetyl-Trp-Gly-Y acetyl-Trp-Gly-Gly-Y
acetyl-Trp-Ala-Y
Acetyl-Trp-Ala-Gly-Y Bz-Tyr-Phe-Y
Bz-Phe-Try-Y
Bz-Tyr-Tyr-Y E. Trypsin Z-Arg-Y
Bz-Arg-Y
(p-R)-Bz-Phe-Val-Arg-Y
N-(acetyl)-Phe-Val-Arg-Y
cyclohexylcarbonyl-Phe-Val-Arg-Y
N-(tosyl)-Phe-Val-Arg-Y
N-(p-aminobenzoyl)-Phe-Val-Arg-Y
Phe-Val-Arg-Y
Bz-Phe-Val-Arg-Y
Phe-Val-Arg-Y
Bz-(D)Phe-Val-Arg-Y
Tyr-Val-Arg-Y
N-(B)-Tyr-Val-Arg-Y
(4-aminocyclohexylcarbonyl)-Phe-Val-Arg-Y
(4-amino butyryl)-Phe-Val-Arg-Y
2-(4-amino phenyl)acetyl-Phe-Val-Arg-Y
N-(Bz)-Phe-Val-Lys-Y
N-(Bz)-Leu-Leu-Arg-Y
β-cyclohexyl-Ala-Val-Arg-Y
N-(Bz)-β-cyclohexyl-Ala-Val-Arg-Y
N-(Bz)(N-cyclohexyl)-β-Ala-Val-Arg-Y
N-(Bz)-Val-Arg-Y
N-(Bz)-Val-Val-Arg-Y
N-(Bz)-Leu-Val-Arg-Y
N-(Bz)-Ile-Val-Arg-Y
N-(Bz)-Val-Ile-Arg-Y
N-(Bz)-Ile-Ile-Arg-Y
N-(Bz)-Leu-Ile-Arg-Y
Cbo-Arg-Arg-Arg-Y
<Glu-Gly-Arg-Y
Bz-Ile-Glu-Gly-Arg-Y
(D)Ala-Ala-Arg-Y
(D)Leu-Gly-Arg-Y
(D)Leu-Ile-Arg-Y
(D)Leu-Val-Arg-Y
(D)Leu-Val-Lys-Y
(D)Pip-Phe-Arg-Y
(D)Leu-Leu-Arg-Y
Z-Ala-Arg-Arg-Y F. Thrombin Bz-Phe-Val-Arg-Y sarcosyl-Pro-Arg-Y
tosyl-Gly-Pro-Arg-Y
(D)Phe-Pip-Arg-Y
(D)Phe-Pro-Arg-Y
Val-Pro-Arg-Y
Ile-Pro-Arg-Y
Gly-Val-Arg-Y
Phe-Pro-Arg-Y
tosyl-Gly-Pro-Arg-Y
Boc-Val-Pro-Arg-Y
Bz-Gly-Pro-Arg-Y
Z-Gly-Pro-Arg-Y
Gly-Pro-Arg-Y
(D)Phe-Val-Arg-Y
(D)Val-Pip-Arg-Y
(D)Tyr-Pip-Arg-Y
(D)Phe-Aze-Arg-Y
N-(Bz)-Phe-Val-Arg-Y
(D)Val-Pro-Arg-Y
(D)Val-Leu-Arg-Y
(D)Pro-Phe-Lys
Gly-Arg-Y
CbO-Gly-Pro-Arg-Y
CbO-Pro-Phe-Arg-Y
CbO-Pro-Arg-Y
Boc-Val-Pro-Arg-Y
(D)Ala-Pro-Arg-Y
(N-R)-Ala-Pro-Arg-Y
(N-R)-(D)Ala-Pro-Arg-Y
CbO-Sar-Pro-Arg-Y
tosyl-Sar-Pro-Arg-Y
Bz-Sar-Pro-Arg-Y
β-Ala-Pip-Arg-Y
β-Ala-Aze-Arg-Y
β-Ala-Pro-Lys-Y
β-Ala-Pip-Lys-Y
β-Ala-Pro-Orn-Y
β-Ala-Pip-Orn-Y
β-Ala-Aze-Orn-Y
α-aminobutyryl-Pro-Arg-Y
α-aminobutyryl-Pip-Arg-Y
α-aminobutyryl-Aze-Arg-Y
α-aminobutyryl-Pro-Lys-Y
α-aminobutyryl-Pip-Lys-Y
α-aminobutyryl-Pro-Orn-Y
α-aminobutyryl-Pip-Orn-Y
α-aminobutyryl-Aze-Orn-Y
α-aminobutyryl-Aze-Lys-Y
phenoxyacetyl-Pro-Arg-Y
phenoxyacetyl-Pip-Arg-Y
phenoxyacetyl-Aze-Arg-Y
phenoxyacetyl-Pro-Lys-Y
phenoxyacetyl-Pip-Lys-Y
phenoxyacetyl-Aze-Lys-Y
phenoxyacetyl-Pro-Orn-Y
phenoxyacetyl-Aze-Orn-Y
phenoxyacetyl-Pip-Orn-Y
N-[3-R-2-(3-phenyl-2-benzamido-thio-R)-butanoyl]-Arg-Y
N-[4-RO-benzenensulfonyl]-Arg-Y
N-[3-R-2-(3-phenyl-2-benzamido-thio-R)-butanoyl]-N-4(RO-benzensulfonyl)-Arg-Y
N-Z-Lys-Y
N-Z-Orn-Y
N-[3-R-3-(3-phenyl-2-benzamido-thio-R)-butanoyl]-N-Z]-Lys-Y
N-[3-R-3-(3-phenyl-2-benzamido-thio-R)-butanoyl]-N-Z]-Orn-y
N-[3-R-2-(3-phenyl-2-benzamido-thio-R)-butanoyl]-Lys-Y
N-[3-R-2-(3-phenyl-2-benzamido-thio-R)-butanoyl]-Orn-Y β-Ala-Pro-Arg-Y

G. Factor XA

Bz-Ile-Glu-(γ piperidyl)-Gly-Arg-Y
Bz-Ile-Glu-Gly-Arg-Y
Boc-Ser-Gly-Arg-Y
Boc-Ile-Glu-Gly-Arg-Y
Bz-Ile-Gly-Gly-Arg-Y
Ile-Glu-Gly-Arg-Y
Boc-Ser-(O benzoyl)-Gly-Arg-Y
(D)Ile-Gly-Gly-Arg-Y
Z-Leu-Gly-Arg-Y
Bz-Val-Glu-Gly-Arg-Y
Bz-Leu-Glu-Gly-Arg-Y
Bz-Leu-Asp-Gly-Arg-Y
Z-Gly-Ala-Arg-Y
Phe-Glu-Gly-Arg-Y
Bz-Val-Glu-Gly-Arg-Y
Bz-Ile-Gln-Gly-Arg-Y
Phe-Glu-Gly-Arg-Y
Bz-Ile-Glu(OR)-Gly-Arg-Y Bz-Ile-Glu(O cyclohexyl)-Gly-Arg-Y Bz-Ile-Glu[OC$_2$H$_4$N(CH$_3$)$_2$]-Gly-Arg-Y $$Bz-Ile-Glu[\overset{O}{\overset{\|}{C}}-NH-CH(CH_3)_2]-Gly-Arg-Y$$

Bz-Ile-Asp(β morpholinyl)-Gly-Arg-Y $$Bz-Ile-Glu[\overset{O}{\overset{\|}{C}}-NH(C_2H_4OH)_2]-Gly-Arg-Y$$

Bz-Ile-Asp(OR)Gly-Arg-Y $$Bz-Ile-Asp[\overset{O}{\overset{\|}{C}}-NH-CH(CH_3)_2]Gly-Arg-Y$$

(D)Ile-Glu-Gly-Arg-Y

H. Plasmin (D)Val-Leu-Lys-Y
tosyl-Gly-Pro-Lys-Y
Ala-Phe-Lys-Y
Boc-Val-Leu-Lys-Y
succinoyl-Ala-Phe-Lys-Y
RO-succinoyl-Ala-Phe-Lys-Y
Z-Ala-Ala-Lys-Y
Z-Gly-Gly-Lys-Y
Z-Phe-Phe-Lys-Y
Val-Leu-Lys-Y
Bz-Val-Leu-Lys-Y
Gly-Pro-Lys-Y
Bz-Ile-Leu-Lys-Y
Ile-Leu-Lys-Y
(D)-Ile-Leu-Lys-Y
(D)-Ala-Leu-Lys-Y
Boc-Glu-Lys-Lys-Y
Bz-Leu-Leu-Lys-Y
N-(6-aminohexanoyl)-Phe-Val-Arg-Y
β-cyclohexyl-Ala-Val-Arg-Y
N-(Val)-Leu-Arg-Y N-(Bz)-Ile-Leu-Arg-Y
N-(Bz)-Pro-Phe-Arg-Y
N-(acetyl)-Pro-Phe-Arg-Y
N-(cyclohexylcarbonyl)-Pro-Phe-Arg-Y
N-(4-methyl-Bz)-Pro-Phe-Arg-Y
N-(a-aminocaproyl)-Pro-Phe-Arg-Y
N-(4-aminomethyl-cyclohexylcarbonyl)-Pro-Phe-Arg-Y
N-(4-aminophenyl-acetyl)-Pro-Phe-Arg-Y
N-(CbO)-Pro-Phe-Arg-Y
N-(Bz)-Pro-$\beta$-cyclohexylAla-Arg-Y
N-(Bz)-Pro-Tyr-Arg-Y
N-(Bz)-Pro-Phe-Gly-Arg-Y
Boc-Phe-Gly-Lys-Lys-Y
Boc-Phe-Glu-Lys-Y
Boc-Ile-Glu-Lys-Y
Z-Ala-Ala-Arg-Y
Phe-Phe-Lys-Y
(D)Phe-Phe-Lys-Y
N-(R)-(D)-Phe-Pro-Lys-Y
N-(R)-Phe-Pro-Lys-Y
N-(R)-Ala-Pro-Lys-Y
Sar-Pro-Lys-Y
Sar-Pro-Arg-Y
N-(R)-(D)-Phe-Pro-Arg-Y
N-(R)-Phe-Pro-Arg-Y
N-(R)-Ala-Pro-Arg-Y N$\alpha$-Bz-Pro-Phe-Arg-Y
N$\alpha$-Bz-Pro-Phe-Arg-Y
Z-Val-Val-Lys-Y
Z-Leu-Leu-Lys-Y
Z-Ile-Ile-Lys-Y
Z-Ser-Ser-Lys-Y
Z-Thr-Thr-Lys-Y
Z-Cys-Cys-Lys-Y
Z-Gly-Ala-Lys-Y
Z-Ala-Gly-Lys-Y
Z-Ala-Tyr-Lys-Y
Z-Leu-Met-Lys-Y
Z-Ile-Ala-Lys-Y
Z-Ile-Thr-Lys-Y
Z-Ser-Phe-Lys-Y
Z-Cys-Val-Lys-Y
Z-Met-Tyr-Lys-Y
Z-Phe-Thr-Lys-Y
Z-Tyr-Gly-Lys-Y
Z-Tyr-Met-Lys-Y
N-(CbO)-Gly-Pro-Arg-Y
Gly-Pro-Arg-Y
N-(phenylacetyl)-Glu-Pro-Arg-Y
N-(phenylpropionyl)-Gly-Pro-Arg-Y
N-(cyclohexylcarbonyl)-Gly-Pro-Arg-Y
N-(capryloyl)-Gly-Pro-Arg-Y
N-(benzensulfonyl)-Gly-Pro-Arg-Y
N-(methanesulfonyl)-Gly-Pro-Arg-Y
N-(naphthalenesulfonyl)-Gly-Pro-Arg-Y
N-(isobutyloxycarbonyl)-Gly-Pro-Arg-Y
N-(isobutyloxycarbonyl)-Gly-Pro-Lys-Y
N-(tosyl)-Gly-Pro-Lys-Y
(D)-Ser-Ser-Lys-Y
(D)Thr-Thr-Lys-Y
(D)Cys-Cys-Lys-Y
Sar-Ala-Lys-Y
(D)Ala-Gly-Lys-Y
N-(R)-(D)-Ala-Gly-Lys-Y
N-(R)-Ala-Gly-Lys-Y
(D)-Ile-Thr-Lys-Y
(D)-Ser-Phe-Lys-Y
(D)-Met-Tyr-Lys-Y (D)-Phe-Thr-Lys-Y
glutaryl-Lys-Lys-Y
>Glu-(D)Lys-Y
Ala-(D)Lys-Y
(D)Val-(D)Lys-Y
>Glu-Phe-Lys-Y
(D)Val-Phe-Lys-Y

I. Enterokinase and Related Enzymes

Bz-(Asp)$_4$-Lys-Y
Gly-(Asp)$_4$-Lys-Y
Boc-(Asp)$_4$-Lys-Y
Bz-(Asp)$_4$-Arg-Y
(D)Asp-(Asp)$_3$-Lys-Y
(D)Asp-(Asp)$_3$-Arg-Y
Gly-(Asp)$_4$-Arg-Y
Boc-(Asp)$_4$-Arg-Y

J. Elastase and Related Enzymes succinoyl-Ala-Ala-Ala-Y
acetyl-Ala-Ala-Ala-Y
succinoyl-Ala-Pro-Ala-Y
succinoyl-Ala-Ala-Pro-Val-Y
succinoyl-Ala-Ala-Pro-Leu-Y
acetyl-Ala-Ala-Pro-Ala-Y
glutaryl-(Ala)$_3$-Y
glutaryl-(Ala)$_2$-Y
Glu-Ala-Ala-Y
succinoyl(OMe)-Ala-Ala-Pro-Val-Y
Boc-Ala-Y

K. Subtilisin

Z-Lys-Nle-Arg-Y
Z-Arg-Nle-Nle-Y
Bz-Arg-Val-Leu-Y
Z-Arg-Val-Leu-Y
Asp-Nle-Nle-Y
succinoyl-Nle-Nle-Y
Z-Asp-Pro-Leu-Y
Z-Asp-Nle-Nle-Y
Bz-Phe-Val-Arg-Y

L. Cathepsin B

Z-Val-Lys-Lys-Y
Z-Ala-Arg-Arg-Y
Bz-Ala-Arg-Arg-Y
Bz-Val-Lys-Lys-Y
Bz-Val-Lys-Lys-Arg-Y
Z-Arg-Arg-Y
Z-Val-Lys-Lys-Arg-Y
Z-Ala-Arg-Arg-Y
Phe-Pro-Ala-Met-Y
glutaryl-Gly-Phe-Y
Bz-Arg-Y
Bz-Arg-Gly-Leu-Y
Bz-Gly-Gly-Arg-Y

M. Cathepsin D

<Glu-(D)-Phe-Pro-Phe-Phe-Y
Bz-Arg-Pro-Gly-Phe-Phe-Leu-Y
Bz-Arg-Pro-Gly-Phe-Phe-Pro-Y
<Glu-(D)Phe-Pro-Phe-Phe(D)Phe-Y
<Glu-(D)Phe-Pro-Phe-Phe-Val-(D)Phe-Y
<Glu-(D)Phe-Pro-Phe-Phe-Val-(D)Trp-Y

N. Collagenase and Related Enzymes succinoyl-Gly-Pro-Leu-Gly-Pro-Y
X-Pro-Leu-Gly-Pro-(D)Arg Z-Pro-Ala-Gly-Pro-Y
X-Pro-Gln-Gly-Ile-Ala-Gly-Gln-(D)Arg
X-Pro-Leu-Gly-Ile-Ala-Gly-Gln-(D)Arg
X-Pro-Gln-Gly-Leu-Ala-Gly-Gln-(D)Arg
X-Pro-Ala-Gly-Leu-Ala-Gly-Gln-(D)Arg
X-Pro-Gln-Gly-Ile-Ala-Gly-(D)Arg
X-Pro-Ala-Gly-Ile-Ala-Gly-Gln-(D)Arg
X-Leu-Gly-Pro-(D)Arg
X-Pro-Gln-Gly-Ile-Ala-Gly-Gln-(D)Arg
X-Pro-Gln-Gly-Ile-Ala-Gly-(D)Arg
X-Gln-Gly-Ile-Ala-Gly-Gln-(D)Arg
X-Ala-Gly-Ile-Ala-Gly-Gln-(D)Arg
CbO-Pro-Ala-Gly-Pro-Y
X-Pro-Pro-Gly-Ile-Ala-Gly-Gln-(D)Arg
X-Pro-Leu-Gly-Ile-Ala-Gly-Arg
X-Pro-Leu-Gly-Ile-Ala-Gly-(D)Arg
X-Leu-Gly-Ile-Ala-Gly-Arg
X-Leu-Gly-Ile-Ala-Gly-(D)Arg
Gly-Pro-Leu-Gly-Y O. Urokinase and Other Plasminogen Activators glutaryl-Gly-Arg-Y
Bz-Val-Gly-Arg-Y
Ile-Ile-Arg-Y
Val-Gly-Arg-Y
Boc-Val-Gly-Arg-Y
Bz-Ile-Gly-Arg-Y
Z-Gly-Gly-Arg-Y
Bz-Gly-Gly-Arg-Y
Gly-Gly-Arg-Y
Bz-Leu-Ile-Arg-Y
Bz-Leu-Leu-Arg-Y
Bz-Phe-Leu-Arg-Y
Pro-Gly-Arg-Y
Dns-Gly-Gly-Arg-Y
Dns-Glu-Gly-Arg-Y
<Glu-Gly-Arg-Y
Bz-Leu-Gly-Arg-Y
Bz-Val-Ser-Arg-Y
Bz-Ile-Ser-Arg-Y
Bz-Leu-Ser-Arg-Y
3-Phenylpropionyl-Val-Gly-Arg-Y
2-Phenylacetyl-Val-Gly-Arg-Y
CbO-methylcyclohexyl-Gly-Gly-Arg-Y
methylcyclohexyl-Gly-Gly-Arg-Y
phenethyl-cyclohexyl-Gly-Gly-Arg-Y
methylcyclohexyl-(D)Gly-Gly-Arg-Y
Bz-methylcyclohexyl-(D)Gly-Gly-Arg-Y
CbO-Val-Gly-Arg-Y
CbO-Gly-Arg-Y
CbO-Gly-(tosyl)-Arg-Y
Boc-Glu-Gly-(tosyl)-Arg-Y
acetyl-Glu-Gly-Arg-Y
(D)Ile-Ile-Arg-Y
(D)Phe-Leu-Arg-Y
(D)Pro-Gly-Arg-Y
(D)Leu-Gly-Arg-Y P. Brush Border Endopeptidases glutaryl-(Ala)$_3$-Y
succinoyl-(Ala)$_3$-Y Q. Cathepsin G Z-Gly-Leu-Phe-Y
glutaryl-Gly-Gly-Phe-Y R. Cathepsin C Ser-Tyr-Y

S. DAP-I

Pro-Arg-Y
His-Ser-Y

T. DAP-II

Lys-Ala-Y
Arg-Ala-Y
Gly-Ala-Y
Asp-Ala-Y

U. DAP-III

Arg-Arg-Y

V. DAP-IV

Gly-Pro-Y

W. Horseshoe Crab Clotting Enzyme

Bz-Ile-Glu($\gamma$ OR)-Gly-Arg-Y
Tosyl-Ile-Glu-Gly-Arg-Y
(D)Val-Leu-Gly-Arg-Y
Boc-Val-Leu-Gly-Arg-Y
Boc-Leu-Gly-Arg-Y
Bz-Ile-Glu-Gly-Arg-Y
Glu-Gly-Arg-Y
Bz-Val-Gly-Arg-Y
Boc-Val-Ser-Gly-Arg-Y
Boc-Ser-Gly-Arg-Y
(D)Ser-Gly-Arg-Y
Bz-Val-Leu-Gly-Arg-Y
Z-Val-Leu-Gly-Arg-Y
(D)Val-Ser-Gly-Val-Ser-Gly-Arg
Boc-Ile-Glu-Gly-Arg-Y
glutaryl-Gly-Arg-Y
Boc-Val-Ser-Gly-Arg-Y
Boc-Ser-Gly-Arg-Y
Boc-Val-Leu-Gly-Arg-Y
Boc-Ser(O benzyl)-Gly-Arg-Y
Val-Gly-Arg-Y
<Glu-Gly-Arg-Y
Bz-Val-Gly-Arg-Y
(D)Val-Gly-Arg-Y
(D)<Glu-Gly-Arg-Y
(D)Glu-Gly-Arg-Y X. Post Proline Cleaving Enzyme Z-Gly-Pro-Y
Bz-Gly-Pro-Y
succinoyl-Gly-Pro-Y
X-Gly-Pro
X-Arg-Pro
X-Ala-Pro
X-Lys-Pro
X-Glu-Pro
X-Asp-Pro
X-His-Pro
X-Leu-Pro
X-Ile-Pro
X-Tyr-Pro
X-Trp-Pro
X-Phe-Pro
X-Val-Pro
X-Gln-Pro
X-Asn-Pro
X-Ser-Pro
X-Cys-Pro
X-Thr-Pro

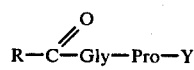

acyl-Arg-Pro-Y
acyl-Ala-Pro-Y
acyl-Lys-Pro-Y
acyl-Glu-Pro-Y
acyl-Asp-Pro-Y
acyl-His-Pro-Y
acyl-Leu-Pro-Y
acyl-Ile-Pro-Y
acyl-Tyr-Pro-Y
acyl-Trp-Pro-Y
acyl-Phe-Pro-Y
acyl-Val-Pro-Y
acyl-Gln-Pro-Y
acyl-Asn-Pro-Y
acyl-Ser-Pro-Y
acyl-Cys-Pro-Y
acyl-Thr-Pro-Y

Y. X-Prolyl Dipeptidyl Aminopeptidase

Gly-Pro-Y
Arg-Pro-Y
Ala-Pro-Y
Lys-Pro-Y
Glu-Pro-Y
Asp-Pro-Y
His-Pro-Y
Leu-Pro-Y
Ile-Pro-Y
Tyr-Pro-Y
Trp-Pro-Y
Phe-Pro-Y
Val-Pro-Y
Gln-Pro-Y
Asn-Pro-Y
Ser-Pro-Y
Cys-Pro-Y
Thr-Pro-Y

Z. Glandular Kallikrein (D)Val-Leu-Arg-Y
(D)Pro-Phe-Arg-Y
Z-Phe-Arg-Y
Leu-Met-Lys-Y
Ser-Leu-Met-Y
Asp-Trp-Arg-Y
Phe-Arg-Y
Z-Pro-Phe-Arg-Y
Val-Leu-Arg-Y
Ile-Leu-Arg-Y
(D)Ile-leu-Arg-Y
acetyl Pro-Phe-Arg-Y
Bz-Pro-Phe-Arg-Y
cyclopentylcarbonyl-Pro-Phe-Arg-Y
acetyl-Phe-Arg-Y
Z-Leu-Gly-Arg-Y

AA. Plasma Kallikrein

N-(caproyl)-Pro-Phe-Arg-Y
N-(3-phenylpropanoyl)-Pro-Phe-Arg-Y
N-(tosyl)-Pro-Phe-Arg-Y
N-(Boc)-Leu-Gly-Arg-Y
CbO-Phe-Arg-Y
Phe-Arg-Y

BB. Angiotensin Converting Enzyme

X-Phe-Ser-Pro
X-Gly-Gly-Gly
X-Gly-His-Leu
X-Phe-His-Leu
X-Pro-Phe-Arg
X-Phe-Ala-Pro
X-(D)Phe-Ala-Pro
X-(D)Phe-His-Leu
X-(D)Phe-Ser-Pro
Met-Phe-Gly-Y
Leu-Phe-Gly-Y
X-Phe-Phe-Ala
X-Phe-O-Phe-Ala
X-Gly-O-Gly-Phe
X-Gly-O-Phe-Phe
X-Gly-O-Leu-Ala
X-Gly-Gly-Phe

CC. Oxytocinase cystinoyl-Y

DD. Neutral Protease

R-Gly-Leu-Y
R-Ala-Leu-Y
R-Gly-Phe-Y
furylacryloyl-Gly-Leu-Y
furylacryloyl-Gly-Phe-Y
thienylacryloyl-Gly-Leu-Y
thienylacryloyl-Ala-Leu-Y
thienylacryloyl-Gly-Phe-Y

EE. Proline Endopeptidase

<Glu-His-Pro-Y
<Glu-(benzimidazolyl)His-Pro-Y

In addition, this invention embraces substrates of the general formula

X—(Pep)—Y wherein X and Y have the significance stated above and (Pep) is a residue containing at least 2 aminoacid moieties which may be substituted with simple acyl, acyloxy, alkyl, aryl, alkoxy, aroxy, alkylamino, arylamino, cycloalkyl, cycloalkoxy, cycloalkylamino, cycloalkylcarbonyloxy, alkyloxycarbonyl, aryloxycarbonyl, cycloalkyloxycarbonyl heterocyclic and like groups of the nature exemplified above in Table 2. Table 3 exemplifies some of the X-(Pep)-Y substrates which can be used in various circumstances; e.g., (1) Where the differently labelled ends of the substrate molecule have specificity for different enzymes. For example, some of the named X-(Pep)-Y substrates can be used to determine post proline cleaving enzyme and proline carboxypeptidase sequentially in the same sample provided that the radiolabels in each of X and Y are different from each other, and (2) Where in very precise work or for special research reasons, it is desired to measure the radioactivity of both the cleaved leaving group from the enzyme—substrate hydrolysis reaction and the enzymatic reaction product with the cleaved residual group.

TABLE 3

| | | |
|---|---|---|
| X—Gly—Pro—Y | X—Gly—Leu—Y | X—Gly—Trp—Y |
| X—Arg—Pro—Y | X—Ala—Leu—Y | X—Gly—Tyr—Y |
| X—Ala—Pro—Y | X—Gly—Phe—Y | X—Gly—Ala—Y |
| X—Lys—Pro—Y | X—Ser—Tyr—Y | X—Gly—Lys—Y |

TABLE 3-continued

| | | |
|---|---|---|
| X—Glu—Pro—Y | X—Pro—Arg—Y | X—Ala—Trp—Y |
| X—Asp—Pro—Y | X—His—Ser—Y | X—Ala—Tyr—Y |
| X—His—Pro—Y | X—Lys—Ala—Y | X—Ala—Ala—Y |
| X—Leu—Pro—Y | X—Arg—Ala—Y | X—Ala—Lys—Y |
| X—Ile—Pro—Y | X—Gly—Ala—Y | X—Phe—Tyr—Y |
| X—Tyr—Pro—Y | X—Asp—Ala—Y | X—Phe—Trp—Y |
| X—Trp—Pro—Y | X—Asp—Arg—Y | X—Phe—Ala—Y |
| X—Phe—Pro—Y | X—Arg—Arg—Y | X—Tyr—Tyr—Y |
| X—Val—Pro—Y | X—Gly—Phe—Y | X—Tyr—Trp—Y |
| X—Gln—Pro—Y | X—Gly—Arg—Y | X—Trp—Trp—Y |
| X—Asn—Pro—Y | X—Ala—Phe—Y | X—Tyr—Ala—Y |
| X—Ser—Pro—Y | X—Ala—Arg—Y | X—Phe—Lys—Y |
| X—Cys—Pro—Y | X—Phe—Phe—Y | X—Trp—Lys—Y |
| X—Thr—Pro—Y | X—Phe—Arg—Y | X—Tyr—Lys—Y |

Other X-(Pep)-Y substrates within the scope of this invention are readily apparent.

The substrates of this invention are synthesized according to conventional peptide synthesis techniques. In general, the substrates of this invention may be prepared similarly to the analogous chromogenic or fluorogenic substrates. According to one method, a benzylamide compound is attached to the C-terminal amino acid group. The benzylamide group at the same time protects the C-terminal carboxyl group during the stepwise attachment of the amino acids in the process of building up the peptide chain. The other protecting groups are selectively eliminated from the end product without the benzylamide group being affected. See *Peptide Synthesis*, Interscience Publishers (1966) for a general description of peptide synthesis.

Typically, the benzylamino group can be coupled to the finished peptide chain before the protecting groups, if any, are removed. Benzylamine may also be attached to the C-terminal amino acid, followed by coupling of this product to the remainder of the peptide chain. Such chain may be prepared by step-wise attachment of amino acids to the growing chain.

The preferred method of forming the benzoyl or p-OH-phenylpropanoyl derivatives is to couple the benzoyl or p-OH-phenylpropanoyl group to the N-terminal amino acid of the completed peptide chain. Alternatively, the benzoyl or p-OH-phenylpropanoyl group is coupled to an active ester of a salt of the N-terminal amino acid. In the latter case, the benzoyl or p-OH-phenylpropanoyl group serves to protect the α-amino group during the completion of the peptide chain by step-wise techniques or fragment condensation. Both methods protect against racemization of the N-terminal amino acid residue.

Generally, ortho-, meta- or para-iodobenzoic acid is used as the precursor of the benzoyl group, but the corresponding bromo or chloro-derivatives can be used as well. The ortho-, meta-, or para-halobenzylamine is used as the precursor of the benzylamide group. Any of these compounds can be radiolabelled to contain [3H] at high specific radioactivity by catalytic dehalogenation in tritium gas. In the latter method, the benzoyl or benzylamide derivative is added to a solvent such as dimethylformamide/$H_2O$ (1:1). Palladium on a catalytic support, such as, e.g., calcium carbonate or charcoal, and tritium gas are added and the mixture is stirred under ½ to 1 atmosphere pressure for 1 or more hours. The catalyst is removed and the desired product is isolated. The p-OH-phenylpropanoyl group is generally used as its $^{125}$I mono- or di-substituted derivative (either 3' or 3',5'-$^{125}$I in respect to the phenyl ring). The active ester derivative is available commercially (e.g., Bolton-Hunter reagent, New England Nuclear Corp.). Alternatively, $^{125}$I or $^{131}$I can be introduced into the p-OH-phenyl ring after completion of synthesis of p-OH-phenylpropanoylpeptide with an oxidizing agent such as Chloramine T. Another alternative is to exchange the iodo-, bromo- or chloro-functions for [3H] atoms by dehalogenation in tritium gas as described above.

For protecting the N α-amino groups during the step-wise synthesis of the peptide chain conventional protective groups known to protect amino groups and to be split off selectively can be used. Such protective groups include in the first place Z, Boc, Ppoc (i.e., phenylisopropyloxycarbonyl), Bpoc (i.e., 2(p-biphenylyl)-isopropyloxy carbonyl, and Fmoc (i.e., 9-fluorenylmethyloxycarbonyl). The α-carboxy group of the amino acids can be activated by several known methods, e.g., by preparing the p-nitrophenyl ester, pentachlorophenyl ester, or N-hydroxysuccinimide ester derivatives and isolating these derivatives, or by preparing in situ the acid halides, acyl azides or acid anhydrides which may be either symmetrical or asymmetrical.

The activation of the carboxy group can also be achieved by means of a carbodiimide such as N,N'-dicyclohexylcarbodiimide (DCC) or ethoxycarbonyl-2-ethoxy-1,2-dihydroquinoline (EEDQ).

The C-terminal carboxy group in the peptide derivatives is protected during the step-wise synthesis of the required peptide chain by means of a benzylamide group or by conversion into the methyl, ethyl or tert-butyl ester.

The other active free groups which do not participate in the synthesis of the peptide chain can be blocked by known methods. Thus, the δ-guanidino group of arginine may be protected by $NO_2$ or Tos or a salt, whereas the ε-amino group of lysine may be protected by a Z, Boc or Fmoc group.

The preparation and use of the substrates of the invention are described in a more detailed manner in the following examples.

Throughout the examples, the following solvent systems were used in the volume ratios shown for the analytical steps represented by the symbols shown below:

Paper Electrophoresis measurements pH 1:9-formic acid/acetic acid/water (15:10:75)
pH 5:0-1,3 propanediol/acetic acid/pyridine/water 100/6/8.5/885.5)

Thin layer chromatography measurements

| | Solution |
|---|---|
| 1 | methanol/chloroform (1/1) |
| 2 | benzene/water/acetic acid (9/1/9) |
| 3 | acetic acid/water/butanol (26/24/150) |
| A | butanol/pyridine/acetic acid/water (15/10/3/12) |
| B | chloroform/methanol/ammonium hydroxide (60/45/20) |
| C | butanol/acetic acid/ethylacetate/water (1/1/1/1) |
| D | ethyl acetate/acetic acid/pyridine/water (5/1/5/3) |

EXAMPLE 1

Synthesis of Tos-Gly-Pro-Arg-[3H]benzylamide

N α-Boc-Arg(tosyl)-OH, 10 mmoles, was mixed with 10 mmoles of 1-hydroxybenzotriazole (HOBt) in 25 ml of redistilled tetrahydrofuran (THF), and the solution was stirred at −5° C. Dicyclohexylcarbodiimide (DCC), 10 mmoles, in 5 ml of precooled $CH_2Cl_2$ was added, and the solution was stirred at $-5°$ C. for 10 minutes. A cool solution of 10 mmoles of meta-iodobenzylamine in 10 ml of THF, previously neutralized with N-ethyl morpholine, was added, and stirring at $-5°$ C. was continued for ½ hour. The reaction mixture was stirred at 4° C. overnight. The precipitate was removed by filtration and was washed with ethyl acetate. The solvent of the first filtrate was removed with a rotary evaporator at 40° C. The ethyl acetate wash was added to the residue. The cooled organic solution was washed successively with saturated NaCl, 1M citric acid, saturated NaCl, 1N $NaHCO_3$ and then with saturated NaCl. The organic phase was dried over anhydrous $MgSO_4$. Solvent of the filtered solution was removed with a rotary evaporator to yield 4 g of the product, Boc-Arg(Tos)-3-iodo-benzylamide as a crystalline material. After recrystallization in dichloromethane/isopropanol, 3.47 g of white crystals were obtained of m.p. 159°-159.5° C. Analysis for $C_{25}H_{34}N_5ISO_5$ calcd. C=46.66, H=5.32; N=10.88, I=19.72, S=4.98; found C=46.64, H=5.26, N=10.75, I=19.44, S=4.99. Thin layer chromatography gave values $R_f(1)=0.76$, $R_f(2)=0.77$, $R_f(3)=0.69$.

The Boc group was removed using trifluoroacetic acid (TFA) in the presence of anisole to yield Arg(Tos)-3-iodobenzylamide.TFA. The TLC analysis gave value of $R_f(1)=0.77$, $R_f(2)=0.66$ and $R_f(3)=0.71$. Elementary analysis for $C_{26}H_{36}N_5ISO_5$-calcd. C=47.50, H=5.52, N=10.65, I=19.30, S=4.88; found C=47.68, H=5.57, N=10.46, I=18.67. To the latter product, 1.0 mmole in 2 ml of dimethylformamide (DMF) solution, neutralized with N-ethyl morpholine, was added 1.0 mmole of the N—OH-succinimide ester of Boc-Pro in 1 ml of DMF. HOBt, 1 mmole, was added and the solution was stirred at 0° C. for 30 minutes and then at room temperature overnight. The reaction was terminated by adding N,N-dimethyl-1,3-propanediamine. DMF was removed by evaporation at 40° C. The residue was dissolved in ethyl acetate, and the solution was washed until neutral. The ethyl acetate layer was dried over anhydrous $MgSO_4$. After filtration, solvent was removed by evaporation to yield Boc-Pro-Arg(Tos)-3-iodo-benzylamide, 648 mg, as a foam-like material. The product behaved like a pure substance in 3 thin layer chromatography systems giving values $R_f(1)=0.74$, $R_f(2)=0.63$, $R_f(3)=0.65$.

The Boc group of Boc-Pro-Arg(Tos)-3-iodo-benzylamide was removed by reacting 620 mg of the latter compound in 2 ml of 7M HCl in THF for 1 hour. The desired product was crystallized by adding anhydrous ether and was collected by filtration. The crystals were washed with ether and then dried in a vacuum desiccator. The compound behaved as a pure substance on paper electrophoresis at pH 5. Amino acid analysis: Pro 1.00, Arg 0.96.

H-Pro-Arg(Tos)-3-iodo-benzylamide.HCl, 503 mg, and 0.315 ml of triethylamine, were dissolved in 3 ml of $CHCl_3$ (redistilled over $NaHCO_3$). To this solution was added 372 mg of the acid chloride of Tos-Gly in 2 ml of $CHCl_3$. The solution was stirred in an ice bath for 30 minutes and at room temperature overnight. Triethylamine, 0.38 ml, and 174 mg of the acid chloride of Tos-Gly in 7 ml of $CHCl_3$ was added, and the resulting solution was stirred for 2 hours. Ethyl acetate, 40 ml, was added and a white precipitate formed. The precipitate was removed by filtration and was washed with dilute HCl, $H_2O$ and then with ethyl acetate. The solvent of the filtrate was removed with a rotary evaporator to yield 382 mg of foam-like solid. Crude product, 350 mg, was mixed with 400 μl of anisole and 5 ml of anhydrous HF at 0° C. for 1 hour. The residue was dissolved in 30% acetic acid, extracted twice with ether and then freeze dried. The dry powder was dissolved in a small amount of acetic acid and applied to a column (1.2×99 cm) of Sephadex G-10 equilibrated and eluted with 40% acetic acid. Fractions (each of 2.85 ml) were collected. Fractions 21-28 were lyophilized to yield 251 mg of product. The product was further purified by partition chromatography (Sephadex G-25 developed with butanol/acetic acid/$H_2O$; 4:1:5). The final product (151 mg), Tos-Gly-Pro-Arg-3-iodo-benzylamide, behaved as a single substance in 3 thin layer chromatography systems. Amino acid analysis: Gly 0.93, Pro 1.05, Arg 1.00. Paper electrophoresis $E_{Arg}(1.9)=0.25$; $E_{Arg}(5.0)=0.58$. Thin layer chromatography: $R_f(A)=0.57$, $R_f(B)=0.60$, $R_f(C)=0.55$.

Tos-Gly-Pro-Arg-3-iodo-benzylamide, 10.56 mg, was dissolved in 2 ml of DMF/$H_2O$ (1:1). Palladium on calcium carbonate, 10.56 mg, was added and then 10 Ci of tritium gas was introduced into the reaction vessel. The reaction mixture was stirred at room temperature for 4 hours. The catalyst was removed by filtration and was washed with DMF/$H_2O$ (1:1). Labile tritium was removed by repeated freeze drying. The specific radioactivity of Tos-Gly-Pro-Arg-3-[$^3$H]-benzylamide was computed to be 24 Ci/mmole.

EXAMPLE 2

Synthesis of [$^3$H]benzoyl-Phe-Arg

A solution of 20 mmoles of Boc-L-Phe-OH in 60 ml of redistilled ethyl acetate is cooled to $-5°$ C., and 21 mmoles of DCC is added. The solution is stirred at $-5°$ C. for 10 minutes and then 20.5 mmoles of 2,4,5-trichlorophenol is added. Stirring at $-5°$ C. is continued for 1 hour, at 0° C. for two more hours and then at 4° C. overnight. Acetic acid, 1 ml, is added and the solution stirred for 1 hour. The precipitate is removed by filtration and washed with ethyl acetate. The combined filtrates are cooled and then washed successively with 0.5M HCl, saturated NaCl, 1N $NaHCO_3$ and saturated NaCl. The organic phase is dried over anhydrous $MgSO_4$, and after filtration the solvent of the organic phase is removed with a rotary evaporator. The product, the trichlorophenol ester of Boc-L-Phe, is recrystallized from a small volume of ethyl acetate plus ether and petroleum ether (30°-60° C.) to yield 8.0 g of white needles. Infrared spectroscopy: urethane carbonyl at 1710 cm$^{-1}$, phenyl ester carbonyl at 1775 cm$^{-1}$. Electrophoresis at pH 1.9 and 5 showed only one substance, which is unreactive with ninhydrin but reactive with $Cl_2$/o-tolidine reagents.

The above product, 4 g, is dissolved in 15 ml of ethyl acetate and cooled in an ice bath. To this solution is added 40 ml of ethyl acetate saturated with hydrogen chloride, and the mixture is stirred at 0° C. for 1 hour. Ether, 20 ml, is added and the mixture was left at 0° C. for 1 hour. The crystalline product is collected by filtration, washed with ether and then dried in a vacuum desiccator over NaOH and $P_2O_5$ to yield 3.4 g of solid. The product, the trichlorophenyl ester of HCl.Phe, is recrystallized from methanol and diethyl ether to yield 2.7 g.

N-(4-iodo-benzoyl)-L-Phe-OTCP (OTCP denotes the trichlorophenyl ester) is formed by dissolving 5 mmoles of HCL.Phe-OTCP in 50 ml of ether at 0° C. with vigorous stirring. To this solution is added 4-iodobenzoyl chloride (7.4 mmoles). Then a pre-cooled solution of 11.9 mmoles of $NaHCO_3$ in 15 ml of $H_2O$ is added step-wise over 20 minutes. Ethyl acetate, 30 ml, is added, and the mixture is stirred at 0° C. for 1 hour and then at room temperature for 1 hour. Crystallization proceeds during the reaction, and the crystals are collected by filtration and are washed with $H_2O$ (3 ml, 4 times) and then ethyl acetate. The crystals are dried in a vacuum desiccator.

The 4-iodo-benzoyl-Phe-Arg is prepared by reacting 0.15 mmoles of 4-iodo-benzoyl-Phe-OTCP and 0.15 mmoles of HOBt in 1 ml of DMF at 0° C. with 0.15 mmoles of H-Arg($NO_2$)-benzyl ester in 1.5 ml of DMF (the latter solution neutralized with N-ethyl morpholine) at 0° C. for 30 minutes and at room temperature overnight. Solvent is removed with a rotary evaporator. The residue is dissolved in ethyl acetate and the solution is washed until neutral. The organic phase is dried over anhydrous $MgSO_4$, THF is added and $MgSO_4$ is removed by filtration. Solvent is removed with a rotary evaporator. The $NO_2$- and benzyl ester-protecting groups are removed by anhydrous HF in the presence of anisole as described in Example 1 to yield 4-iodo-benzoyl-Phe-Arg. Amino Acid Analysis: Phe 1.04; Arg 1.00. Paper electrophoresis, $E_{Arg}(1.9)=0.83$. Thin layer chromatography: $R_f(1)=0.32$; $R_f(2)=0.61$; $R_f(3)=0.31$. The latter compound is dehalogenated in tritium gas as described in Example 1 to yield 4-[$^3$H]-benzoyl-Phe-Arg, the named compound.

EXAMPLE 3

Synthesis of Ala-Ala-Phe-[$^3$H]benzylamide

Phe-3-iodobenzylamide is prepared by coupling Aoc-Phe-OH with meta-iodobenzylamine using DCC and 1-HOBt. The product is deprotected with ethanolic HCl to yield Phe-3-iodobenzylamide.HCl. Boc-Ala is coupled to this product in the presence of 1-HOBt in DMF and DCC at about 0° C. with N-ethyl morpholine as base. The product is deprotected by treatment with anhydrous HCl to yield Ala-Phe-3-iodobenzylamide. Boc-Ala is coupled to this product and the resulting product deprotected in the same manner to yield Ala-Ala-Phe-3-iodobenzylamide. The named substrate is obtained by substantially following the method described in Example 1 for catalytic tritation.

EXAMPLE 4

Synthesis of (D)Phe-Pip-Arg-[$^3$H]benzylamide

H-Arg(Tos)-3-iodo-benzylamide.HCl is prepared as described in Example 1. Boc-Pip-OTCP ester is prepared essentially as described for Boc-Phe-OTCP in Example 2 and is coupled, to H-Arg(Tos)-3-iodo-benzylamide in DMF plus HOBt, with neutralization by N-ethyl morpholine. The Boc-group is removed with trifluoroacetic acid. Pip-Arg(Tos)-3-iodo-benzylamide and HOBt in DMF (neutralized with N-ethyl morpholine) are reacted with Boc-(D)Phe-ONSu ester at −5° C. for 30 min. at 4° C. overnight and at room temperature for 5 hours to yield Boc-(D)Phe-Pip-Arg(Tos)-3-iodo-benzylamide. The Boc- and Tos-groups are removed with anhydrous HF in the presence of anisole, all at 0° C., to yield (D)Phe-Pip-Arg-3-iodo-benzylamide. Paper Electrophoresis: $E_{Arg}(1.9)=0.66$, $E_{Arg}(5.0)=0.91$. Thin layer chromatography: $R_f(A)=0.60$; $R_f(B)=0.86$; $R_f(C)=0.51$. The named compound is obtained by catalytic dehalogenation essentially as described in Example 1.

EXAMPLE 5

Synthesis of [$^3$H]benzoyl-Pro-Leu-Gly-Pro-(D)Arg

Boc-(D)Arg(Tos)-resin is prepared according to the method of Gisin (Helv. Chim. Acta 56, 1476, 1973). The resin is transferred to a shaker vessel of a peptide synthesizer and is washed with $CH_2Cl_2$ for 5 min. The Boc group is removed with 25% trifluoroacetic acid in $CH_2Cl_2$ and then the resin is washed successively with $CH_2Cl_2$, 10% isopropanol in $CH_2Cl_2$, $CH_2Cl_2$, 5% diisopropylethylamine in $CH_2Cl_2$, $CH_2Cl_2$ DMF and then $CH_2Cl_2$. Boc-Pro (2.5 equivalents) and HOBt (2.5 equivalents) in $CH_2Cl_2$ are added and mixed with the resin by shaking for 10 minutes and then DCC in $CH_2Cl_2$ is added to effect coupling. The reaction is allowed to proceed for 2.5 hours. The resin is then washed successively with $CH_2Cl_2$, DMF, and butanol. The Boc group is removed, the resin washed and the next Boc amino acid added to repeat the coupling sequence. After the polypeptide chain is assembled, the N-terminal amino acid residue is coupled with p-iodobenzoyl chloride. The acyl-oligopeptide is cleaved from the resin with anhydrous HF in the presence of anisole. The resin is removed by filtration using 10% acetic acid as solvent for the acyl-oligopeptide. The pure p-iodobenzoyl-Pro-Leu-Gly-Pro-(D)Arg is obtained by conventional chromatography techniques. The named compound is obtained by catalytic dehalogenation in tritium gas essentially as described in Example 1.

EXAMPLE 6

Assay of carboxypeptidase B-like enzyme of human urine

Fresh human urine, 2 liters, is ultrafiltered to 100 ml on a filter with a retention limit of 10,000 molecular weight. The concentrated urinary proteins are washed twice with 100 ml of 0.1M NaCl. Aliquots of the washed urinary proteins (0–50 μl) are transferred to the bottom of 12×75 mm glass test tubes, and the content of each tube is adjusted to 50 μl by adding a sufficient quantity of 0.2M Tris.HCl buffer, pH 7.5, plus 0.1M NaCl. To each tube is added 0.1 μCi of [$^3$H]benzoyl-Phe-Arg in the buffer (approximately 40 nM in the final reaction mixture). The reaction mixture are incubated at 37° C. for 15–120 minutes and the reactions are stopped by adding 1.0 ml of 0.1N HCl. Toluene, 1 ml, is added to each tube and the contents mixed by vortexing. After phase separation, 500 μl of the toluene phase is transferred to a 7 ml scintillation vial containing 4 ml of Riafluor ® (New England Nuclear Corp.). To a separate vial, 50 μl of the buffered substrate is added to 4 ml of RIAfluor. All vials are submitted for liquid scintillation counting. Enzymic activity is manifest in terms of increasing extractability of tritium into toluene. The substrate itself is not partitioned into toluene (less than 2%), but the product, [$^3$H]benzoyl-Phe, is partitioned into toluene to an extent of 70% under our conditions. Total substrate (S) available is measured in c.p.m. of the vial containing 50 μl of substrate in Riafluor. The blank (B) value is obtained by measuring c.p.m. of toluene extractable tritium from reaction mixtures without enzyme. The test samples (T) are those in which some quantity of enzyme was used during incubation and each is measured in terms of toluene extractable [$^3$H].

Thus enzyme activity/ml of urinary protein, [E]/ml, can be estimated from the following equation.

$$[E]/\text{ml} = \frac{\frac{2(T-B)}{S} \times 100}{t \cdot \text{vol.}}$$

where t equals time of incubation in minutes, vol equals the volume in ml. of enzyme added to a given reaction mixture. The term 100 converts the fractional utilization of substrate into percentage. The term 2 corrects for the fact that only one half of each toluene phase is used for liquid scintillation counting.

EXAMPLE 7

Measurement of the $K_m$ and $V_{max}$ of the reaction of human thrombin with (D)Phe-Pro-Arg-[$^3$H]benzylamide (D)Phe-Pro-Arg-[$^3$H]benzylamide, 10 µCi/ml, was mixed with unlabelled (D)Phe-Pro-Arg-benzylamide in 0.15M Tris-HCl buffer, pH 7.75, plug 0.15M NaCl, to give a final substrate concentration of 40 µM. Six serial dilutions in buffer were made to give a range of substrate concentrations of 0.468–40 µM. Each substrate concentration, 200 µl, was mixed with 200 µl of buffer or buffer containing 0.05 units of human thrombin in a 12×75 mm plastic tube. To measure substrate concentration (S), 100 µl of each given substrate concentration was added to a scintillation vial containing 4 ml of RIA-fluor. The blanks (B) were those reaction mixtures containing substrate and buffer but no enzyme. The test samples (T) contained substrate plus enzyme. The test and blank samples were incubated at 37° C. for 5 minutes and then 100 µl (in duplicate) of each reaction mixture was transferred to a 12×75 mm glass test tube containing 1.0 ml of 0.1N NaOH. Benzylamine was separated from substrate by extraction into 1.0 ml of toluene (vortex mixing for 30 sec.). After phase separation, 500 µl of each toluene phase was transferred to a 7 ml scintillation vial containing 5 ml of RIAfluor. Toluene extractable [$^3$H] was measured by liquid scintillation counting. Under our conditions of extraction, less than 3% of substrate is partitioned into toluene and greater than 70% of the benzylamine is partitioned into toluene. Thus velocity of a given reaction can be computed:

$$\text{velocity (nM/min)} = \frac{\frac{2(T-B)}{S_o} \times \text{starting substrate conc. (nM)}}{\text{time in minutes}}$$

The results are shown in the following Table:

| Starting Substrate Concentration (µM) | Velocity (nM/min) |
|---|---|
| 20 | 84 |
| 9.5 | 67 |
| 4.5 | 52 |
| 2.2 | 30 |
| 1.0 | 16 |
| 0.48 | 8.4 |
| 0.23 | 4.2 |

Using the method of Lineweaver and Burk (double reciprocal plot), the following were computed: $K_m$ 6.18 µM, $V_{max}$ 114 nM/min.

EXAMPLE 8

Indirect assays of prothrombin, anti-thrombin III and heparin using (D)Phe-Pip-Arg-[$^3$H]benzylamide

A. Assay of prothrombin

By converting quantitatively prothrombin of a human plasma sample into thrombin, prothrombin is assayed indirectly as thrombin using (D)Phe-Pip-Arg-[$^3$H]benzylamide in an assay analogous to that described in Example 7. The conversion of human prothrombin into thrombin is catalyzed by adding an excess of human factor Xa to a buffered mixture containing dilute human plasma, rabbit brain cephalin and calcium chloride. When the conversion of prothrombin to thrombin is completed (D)Phe-Pip-Arg-[$^3$H]benzylamide is added (0.05 to 0.5 µCi/100 µl), and the mixture is incubated at 37° C. for 5 minutes. Thrombin activity is measured in terms of the rate of release of [$^3$H]benzylamine essentially as described in Example 7.

B. Assay of anti-thrombin III

The anti-thrombin III of human plasma can be measured by reacting a dilute sample of citrated plasma with a standard quantity of thrombin in the presence of an excess of heparin. The thrombin not taken up (residual thrombin) in the thrombin:anti-thrombin III:heparin complex is measured in terms of the rate of release of [$^3$H]benzylamine from (D)Phe-Pip-Arg-[$^3$H]benzylamide. The product can be separated from substrate by extraction, as in Example 7, ion-exchange chromatography, thin layer chromatography, molecular sieving, or reversed phase or partition chromatography techniques well known in the art.

C. Assay of heparin

Heparin is measured by a modification of the method B, above. A sample containing heparin is mixed with a standard quantity of thrombin and an excess of anti-thrombin III. Residual thrombin not taken up in the thrombin:anti-thrombin III:heparin complex is measured in terms of the rate of release of [$^3$H]benzylamine from (D)Phe-Pip-Arg-[$^3$H]benzylamide essentially as described in Example 7. Thus, the residual thrombin activity is inversely proportional to heparin concentration.

EXAMPLE 9

(D)Pro-Phe-Arg-3-[$^3$H]-benzylamide

A. To a solution of 4.5 mmoles of Boc-(D)-Pro in 3 ml of redistilled DMF at −5° C. was added 4.5 mmoles of DCC in 3 ml of cold DMF. Immediately thereafter was added 4.5 mmoles of (L)Phe-benzyl ester.ToSH in 6 ml of DMF neutralized with 0.612 ml of N-ethyl morpholine. The solution was stirred at −5° C. for 30 minutes and then at 4° C. overnight. The resulting mixture was filtered, the precipitate was washed with ethyl acetate, and the combined filtrates were evaporated to dryness at 40° C. The residue was dissolved in ethyl acetate and the solution was washed until neutral. The organic phase was dried over anhydrous MgSO$_4$ and then filtered. The solvent was removed under high vacuum to yield an oil (2.13 g), Nα-Boc-(D)Pro-Phe-Benzyl Ester. Thin layer chromatography: R$_f$(1)=0.73; R$_f$(2)=0.66; R$_f$(3)=0.68.

B. This was dissolved in 60 ml of methanol containing 0.3 ml of acetic acid. Catalyst, 1.1 g of 10% palladium on calcium carbonate, was added and the mixture was hydrogenated (20 p.s.i.) overnight. The catalyst was removed by filtration and was washed with ethyl acetate. The combined filtrates were evaporated to dryness. The residue was dissolved in ethyl acetate, and the solution was washed with $H_2O$ and then saturated NaCl. The organic phase was dried over anhydrous $MgSO_4$ and then filtered. Solvent was removed under reduced pressure. The product, Nα-Boc-(D)Pro-Phe-OH, was crystallized from ethyl acetate/petroleum ether (30°–60° C.) to yield 783 mg of white solid (m.p. 140.5°–141° C.). A second crop of crystals, 58 mg, was obtained to give an overall yield of 51.5%. Analysis for $C_{19}H_{26}N_2O_5$: calc. C 62.97; H 7.23; N 7.73; found C 62.77; H 7.16; N 7.72. Thin layer chromatography: $R_f(1)=0.66$; $R_f(2)=0.64$; $R_f(3)=0.65$.

C. This product, 1 mmole, and 1 mmole of N-OH-succinimide were dissolved in 0.5 ml of DMF and 2 ml of dichloromethane at −5° C. and then 1.1 mmole of DCC in 2 ml of $CH_2Cl_2$ was added. The mixture was stirred at 4° C. overnight. The mixture was filtered, and the precipitate was washed with ethyl acetate. The combined filtrates were worked up as in Step A. The N-OH-Succinimide Ester of Nα-Boc-(D)Pro-Phe was crystallized from ether to yield 412 mg (89.7%) of white crystals (m.p. 165°–166.5° C.). Elementary analysis for $C_{23}H_{29}N_3O_7$: calculated: C=60.12; H=6.36; N=9.14; found: C=59.93; H=6.43; N=9.01.

D. A solution of 0.5 mmoles of Arg(Tos)iodobenzylamide.TFA made as in Example 1 in 1 ml of DMF containing 0.5 mmoles of N-ethyl morpholine at 0° C. was then added to a cold solution of the product of Step C, N-OH-succinimide ester of Boc-α(D)Pro-Phe, in 1 ml of DMF. The solution was stirred in an ice bath for 30 minutes and then at 4° C. overnight. The reaction mixture was worked up as in subparagraph A of this example and the Nα-Boc-(D)Pro-Phe-Arg(Tos)-3-iodo-benzylamide was crystallized from benzene/hexane to yield 335 mg (75.5%), m.p. 97.5°–98.5° C. Elementary analysis for $C_{39}H_{50}N_7SIO_7$-calculated: C=52.76; H=5.68; N=11.04; S=3.61; found: C=52.69; H=5.68; N=10.76; S=3.76. Thin layer chromatography: $R_f(1)=0.86$; $R_f(2)=0.77$; $R_f(3)=0.72$.

E. The product of Step D, 140 mg, was reacted with 3 ml of anhydrous HF, in the presence of anisole (0.15 ml) for 1 hour HF was removed, the product was dissolved in 30% acetic acid, and the solution was freeze-dried to yield 119 mg of a white powder. The crude product was chromatographed on Sephadex G-10 (1.2×99 cm column) developed and eluted with 25% acetic acid. Fractions, 3.3 ml, were collected. Fractions 19–24 were pooled, solvent was removed by rotary evaporation, and the material was applied to Sephadex LH-20 (1.2×95 cm column) developed and eluted with 6% butanol. Fractions (2.35 ml) were collected and the compound, (D)Pro-Phe-Arg-3-iodo-benzylamide, was obtained in fractions 32–36 (92 mg).

Amino acid analysis: Pro 0.99, Phe 1.00, Arg 1.03. The material behaved as a pure substance in three thin layer chromatography systems: $R_f(A)=0.57$; $R_f(B)=0.88$; $R_f(C)=0.49$. Paper Electrophoresis: $E_{Arg}(1.9)=0.69$; $E_{Arg}(5.0)=0.93$.

F. The product of Step E, 10 mg, was dissolved in 2 ml of $H_2O$/DMF (1:1 by vol) and 10 mg of 10% palladium on calcium carbonate was added. The mixture was hydrogenated in 10 Ci of tritium gas at about 1 atmosphere, at room temperature for 4 hours. The catalyst was removed by filtration and washed with $H_2O$/DMF. The combined filtrates were freeze-dried. The residue was dissolved in $H_2O$ and freeze-drying was repeated to remove labile tritium. The compound, (D)Pro-Phe-Arg-3-[$^3$H]benzylamide, was obtained at a specific radioactivity of 25.3 Ci/mmole.

EXAMPLE 10

Synthesis of (D)Phe-Pro-Arg-3-[$^3$H]-benzylamide

A. Nα-Boc-(D)Phe-Pro-benzyl ester was prepared with 2 mmoles of Boc-(D)Phe-OH, 2 mmoles of DCC and 2 mmoles of L-Pro-benzyl ester in dichloromethane essentially by the method described in Example 9, Step A, to yield 786 mg of product. Thin layer chromatography: $R_f(1)=0.75$; $R_f(2)=0.87$; $R_f(3)=0.75$.

B. The benzyl ester was removed as described in Example 9, Step B, to yield 414 mg of Nα-Boc-(D)Phe-Pro (57.9% yield, m.p. 169°–170° C.). Analysis for $C_{19}H_{26}N_2O_5$ (FW 362.4): Calculated C 62.97, H 7.23, N 7.73; found C 62.87, H 7.28, N 7.54. Amino acid analysis: Phe 1.02, Pro 1.00. Thin layer chromatography: $R_f(1)=0.49$; $R_f(2)=0.75$; $R_f(3)=0.57$.

C. Boc-(D)Phe-Pro-OH, 0.45 mmoles, and 0.45 mmoles of HOBt in 2 ml of $CH_2Cl_2$ plus a few drops of DMF were cooled to −5° C. DCC (0.45 mmoles) in 0.5 ml of $CH_2Cl$ was added. H-Arg(Tos)-3-iodo-benzylamide (0.47 mmoles) and 0.47 mmoles of N-ethyl morpholine in 2 ml of $CH_2Cl_2$ were mixed with the first solution. The reaction mixture was stirred at 4° C. overnight. The mixture was then filtered, the precipitate was washed with ethyl acetate and the combined filtrates were worked up as in Example 9, step A. The compound, Nα-Boc-(D)Phe-Pro-Arg(Tos)-3-iodo-benzylamide, was obtained, by evaporation under high vacuum, as a foam-like solid (218 mg). Thin layer chromatography: $R_f(1)=0.77$; $R_f(2)=0.80$; $R_f(3)=0.67$.

D. The product of Step C was reacted with anhydrous HF as described in Example 9, Step E. The named product was purified by column chromatography (Sephadex G-10 developed with 10% acetic acid; partition chromatography on Sephadex G-25 developed with butanol/acetic acid/$H_2O$[4:1:5], and then Sephadex LH-20 developed with 6% butanol). The compound, (D)Phe-Pro-Arg-3-iodo-benzylamide, was obtained in a yield of 68 mg. Thin layer chromatogrphy: $R_f(A)=0.58$; $R_f(B)=0.77$; $R_f(C)=0.49$; $R_f(D)=0.825$. Paper electrophoresis at pH 1.9=0.725 and at pH 5.0=0.90.

E. The compound, (D)Phe-Pro-Arg-3-[$^3$H]-benzylamide, was obtained by catalytic dehalogenation in tritium gas, essentially as described in Example 9, subparagraph E, at a specific radioactivity of 22 Ci/mmole.

EXAMPLE 11

Preparation of (D)Phe-Pro-Arg-benzylamide (D)Phe-Pro-Arg-3-iodo-benzylamide, 10 mg, was dehalogenated as described in Example 9, Step H, using hydrogen gas instead of tritium gas.

EXAMPLE 12

Preparation of (D)Pro-Phe-Arg-benzylamide was prepared, using the procedure of Example 11.

EXAMPLE 13

Kinetics of the reaction of (D)Pro-Phe-Arg-3-[$^3$H]-benzylamide and (D)Pro-Phe-Arg-benzylamide with human urinary kallikrein (D)Pro-Phe-Arg-3-[$^3$H]-benzylamide and (D)Pro-Phe-Arg-benzylamide were dissolved in 0.2M tris-HCl buffer, pH 9.5, to yield a solution of substrate at 1.97 μM ($^3$H at 1,020,000 c.p.m. [58% counting efficiency] per 50 μl). Serial 1:2 dilutions were made in the buffer. Highly purified human urinary kallikrein (prepared by the method of Oza and Ryan, Biochem. J., 171;285–288, 1978) was dissolved in the buffer to a concentration of 160 ng/ml. Each concentration of substrate, 50 μl, was incubated in a 12×75 mm glass tube for 15 minutes at 37° C. with 50 μl of kallikrein. Reactions were stopped by adding 1.0 ml of 0.1M NaOH. Benzylamine was extracted into 1.0 ml of toluene, and half of each toluene phase was submitted to liquid scintillation counting. A sample (500 μl) of a given toluene phase was transferred to a 7 ml liquid scintillation vial containing 4 ml of LSC Formula 947 (New England Nuclear Corp.). To measure any given substrate concentration, 50 μl of the given substrate solution was transferred to a 7 ml scintillation vial containing Formula 947 as indicated above. Results are shown in the Table.

| [S] - μM | V - μM/min |
|---|---|
| 0.986 | 0.0124 |
| 0.466 | 0.0065 |
| 0.231 | 0.0034 |
| 0.115 | 0.0016 |
| 0.055 | 0.000793 |
| 0.0256 | 0.000389 |
| 0.013 | 0.000176 |
| 0.006 | 0.00090 |

By plotting 1/[S] vs. 1/v the $K_m$ was found to be 1.7 μM and the $V_{max}$ was 0.016 μM/min.

EXAMPLE 14

Preparation of [$^3$H]Benzoyl-(D)Phe-Pip-Arg-[$^3$H]Benzylamide (D)Phe-Pip-Arg-[$^3$H]benzylamide of Example 4 is reacted with 4-iodo-benzoic acid chloride essentially according to the method of Example 5. The resulting compound is subjected to dehalogenation in tritium gas according to the method of Example 1 to yield the named compound. Alternatively, 4-iodobenzoic acid chloride can be condensed with (D)Phe-Pip-Arg-3-iodobenzylamide (Example 4) and both halogen atoms removed in tritium gas simultaneously.

EXAMPLE 15

Preparation of [$^{14}$C]Benzoyl-(D)Pro-Phe-Arg[$^3$H]Benzylamide

The acid chloride of [$^{14}$C]benzoic acid and (D)Pro-Phe-Arg[$^3$H]benzylamide or (D)Pro-Phe-Arg-3iodo benzylamide are reacted, to yield the named in compound in the first instance and in the second, a compound which is converted thereto by dehalogenation in tritium gas.

EXAMPLE 16

Preparation of 3-[$^{25}$I]-4-OH-phenylpropanoyl-(D)Pro-Phe-Arg[$^3$H]benzylamide (D)Pro-Phe-Arg[$^3$H]benzylamide is condensed with Bolton Hunter reagent, 3-[$^{25}$I]-4-OH-phenylpropanoic N-OH succinimide ester to give the named compound.

EXAMPLE 17

Preparation of [$^3$H]benzoyl(D)Pro-Phe-Arg-[$^{14}$C)benzylamide

In the method of Example 1, [$^{14}$C]benzylamine is substituted for m-iodobenzylamine. The intermediate product Arg(Tos)-[$^{14}$C]benzylamide.TFA is treated as in steps D and E of Example 9 to yield (D)Pro-Phe-Arg-[$^{14}$C]benzylamide which is then reacted with 4-iodobenzoic acid chloride and dehalogenated with tritium gas to produce the named compound.

The substrates of this invention can be prepared from appropriate starting materials using the general methods described. When the desired radiolabel is $^{14}$C, [$^{14}$C]benzylamine or [$^{14}$C]benzoyl chloride is substituted for the meta-iodobenzylamine or p-iodobenzoyl chloride in the foregoing examples. Tritium can also be inserted similarly by substituting a tritiated benzylamine or benzoyl halide. Bolton-Hunter reagent can be labelled by dehalogenation in tritium and substituted. Substrates can be prepared in which the radiolabel is $^{125}$I or $^{131}$I by substituting 3-hydroxybenzylamine or 4-hydroxybenzylamine for the halobenzylamine in the foregoing examples. The resulting compounds are readily iodinated with $^{125}$I or $^{131}$I by using the chloramine-T method to yield the corresponding [$^{125}$I]- or [$^{131}$I]hydroxybenzylamides. Iodination of 4-hydroxybenzylamides yields 3-iodo- or 3,5-diiodo-4-hydroxybenzylamides. Iodination of the 3-hydroxybenzylamides yields 6-iodo- or 4,6-diiodo-3-hydroxybenzylamides. Pre-radiolabeled Bolton-Hunter reagent can be used similarly.

Each of the substrates of this invention are useful for the quantitative determination of one or more of the proteolytic and peptidase enzymes found in Table 1. These substrates can also be used for indirectly determining proenzymes, e.g., plasminogen and trypsinogen; proenzyme activators and enzyme inhibitors, e.g., antithrombin III, $\alpha_2$-macroglobulin, $\alpha_1$ antitrypsin, and soya bean trypsin inhibitor.

These indirect determinations are effected by first reacting a proenzyme, e.g., plasminogen with an activator, e.g., urokinase, to form quantitatively the enzyme, e.g. plasmin which can be measured as such. The measurement of the activator concentration is carried out indirectly by determining the velocity of the formation of the enzyme from the proenzyme. This velocity is proportional to the activator concentration.

Hydrolysis of the radioactively labelled substrates by the proteolytic or peptidase enzymes results in the formation of a radioactively labelled benzylamide derivative, benzoyl derivative, or hydroxyphenylpropanoyl derivative, depending on the point of cleavage of the particular substrate by the particular proteolytic or peptidase enzyme. The radioactively labelled products are separated from unhydrolyzed substrate and counted using standard techniques.

A typical assay comprises incubating at 37° C. a clinical sample containing a proteolytic or peptidase enzyme with an appropriate substrate at a predetermined pH for a suitable length of time to allow hydrolysis of the substrate. The incubation is stopped by any technique which causes rapid termination of the enzyme-catalyzed reation without significant alteration of the product. The preferred method is to use an excess of NaOH to terminate the reaction when the substrate contains the benzylamide moiety or splits off a benzylamine leaving group and uses an excess of HCl when the substitute contains the X moiety or splits off an X leaving group. The radiolabelled hydrolysis product is then extracted and the amount of radioactivity measured. A standard curve can be constructed by substituting a particular purified proteolytic or peptidase enzyme.

A unit of enzyme, in this system, can be defined as the amount of enzyme required to hydrolyze substrate at an initial rate of 1% per minute at 37° C. This definition is applicable where the concentration of substrate is well below $K_m$ such that hydrolysis is first order with respect to substrate concentration. The number of enzyme units/ml of sample is given by:

$$\frac{\frac{2(\text{Test c.p.m.} - \text{Blank c.p.m.})}{\text{Total Substrate c.p.m.}} \times 100}{\text{Incubation time (min)} \times \text{vol. of enzyme in ml.}}$$

when 1.0 ml of solvent is used for the extraction and an aliquot of 0.5 ml is taken for counting. The blank c.p.m. value is determined in a control reaction lacking enzyme but otherwise treated identically.

A more accurate computation of enzymic activity, [E], can be obtained using the integrated form of the first order reaction equation:

$$[E] = \frac{1}{kt} \ln \frac{S}{S - P}$$

where k is a reaction constant (0.01 by our definition of units, supra) t is time in minutes, S is the initial substrate concentration and P is the product concentration at time t.

While the invention has been described in connection with specific embodiments thereof, it will be understood that it is capable of further modifications and this application is intended to cover any variations, uses, or adaptation of the invention following, in general, the principles of the invention and including such departures from the present disclosure as come within known or customary practice within the art to which the invention pertains and as may be applied to the essential features hereinbefore set forth, and as fall within the scope of the appended claims.

What is claimed is:

1. A compound of the general formula X-T, W-Y or X-(Pep)-Y wherein
    X is a radiolabelled benzoyl or hydroxyphenylpropanoyl group,
    T is the amino acid or peptide residue of a known chromogenic or fluorogenic substrate containing at least one amino acid moiety and having a free terminal —NH— group which forms an amido bond with X, which residue may be substituted with one or more organic groups,
    W is the amino acid or peptide residue of a known chromogenic or fluorogenic substrate containing at least one amino acid moiety other than the aspartyl or lysyl moiety and having a free terminal  group which forms an amido bond with Y, which residue may be substituted with one or more organic groups,
    Y is a radiolabelled benzylamine group, and
    (Pep) is difunctional or polyfunctional peptide residue from a known chromogenic or fluorogenic substrate containing at least two amino acid moieties in peptide linkage with one another and having a free terminal —NH— group which forms an amido bond with X and a free terminal  group which forms an amido bond with Y, which residue may be substituted with one or more organic groups.

2. A compound according to claim 1 in which the radiolabel is selected from $^3$H, $^{14}$C, $^{125}$I and $^{131}$I.

3. A compound according to claim 1 of the general formula X-(Pep)-Y wherein each of X and Y contains a different radiolabel.

4. A compound according to claim 3 wherein one of X and Y contains $^3$H as a radiolabel and the other contains $^{14}$C.

5. A compound according to claim 1 wherein the T, W or Pep group contains not more than two organic substituents which may be alkyl of 1-5 carbon atoms, aryl selected from phenyl, and naphthyl, cycloalkyl of 3-6 carbon atoms, heterocyclic groups containing 4-6 members, combinations of any two of the foregoing groups and the oxy, carbonyl, carbonyloxy, amino, amido and thioether derivatives of any of them.

6. A compound according to claim 1 of the general formula X-T selected from the group of compounds of that formula which are listed in Table 2 of the specification.

7. A compound according to claim 1 of the general formula W-Y selected from the group of compounds of that formula which are listed in Table 2 of the specification.

8. A compound according to claim 1 of the general formula X-(Pep)-Y selected from the group of compounds listed in Table 3 of the specification.

9. A compound according to claim 1 of the formula Tos-Gly-Pro-Arg-[$^3$H]benzylamide.

10. A compound according to claim 1 of the formula [$^3$H]benzyl-Phe-Arg.

11. A compound according to claim 1 of the formula Ala-Ala-Phe-[$^3$H]benzylamide.

12. A compound according to claim 1 of the formula (D)Phe-Pip-Arg-[$^3$H]benzylamide.

13. A compound according to claim 1 of the formula [$^3$H]benzoyl-Pro-Leu-Gly-Pro-(D)Arg.

14. A compound according to claim 1 of the formula (D)Phe-Pro-Arg-3-[$^3$H]benzylamide.

15. A compound according to claim 1 of the formula (D)Pro-Phe-Arg-3-[$^3$H]benzylamide.

16. A compound according to claim 1 of the formula [$^3$H]benzoyl-(D)Phe-Pip-Arg-[$^3$H]benzylamide.

17. A compound according to claim 1 of the formula [$^{14}$C]benzoyl-(D)Pro-Phe-Arg-[$^3$H]benzylamide.

18. A compound according to claim 1 of the formula [$^3$H]benzoyl-(D)Pro-Phe-Arg-[$^{14}$C]benzylamide.

* * * * *